US007807620B2

(12) United States Patent
Lustbader

(10) Patent No.: US 7,807,620 B2
(45) Date of Patent: *Oct. 5, 2010

(54) LONG-ACTING FOLLICLE STIMULATING HORMONE ANALOGUES AND USES THEREOF

(75) Inventor: Joyce Lustbader, Tenafly, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 957 days.

This patent is subject to a terminal disclaimer.

(21) Appl. No.: 11/490,825

(22) Filed: Jul. 21, 2006

(65) Prior Publication Data

US 2008/0234186 A1    Sep. 25, 2008

Related U.S. Application Data

(63) Continuation of application No. 10/112,321, filed on Mar. 27, 2002, now Pat. No. 7,081,446, which is a continuation-in-part of application No. 10/062,910, filed on Jan. 31, 2002, now abandoned.

(51) Int. Cl.
*A01N 37/18* (2006.01)
(52) U.S. Cl. ........................................................ 514/2
(58) Field of Classification Search .................. None
See application file for complete search history.

(56) References Cited

U.S. PATENT DOCUMENTS

| | | | |
|---|---|---|---|
| 4,179,337 A | 12/1979 | Davis et al. | |
| 5,177,193 A | 1/1993 | Boime et al. | |
| 5,270,181 A | 12/1993 | McCoy et al. | |
| 5,272,070 A | 12/1993 | Lehrman et al. | |
| 5,359,033 A | 10/1994 | Cate et al. | |
| 5,585,345 A | 12/1996 | Boime | |
| 5,661,126 A | 8/1997 | Donahoe et al. | |
| 5,712,122 A | 1/1998 | Boime et al. | |
| 5,728,381 A | 3/1998 | Wilson et al. | |
| 5,759,818 A | 6/1998 | Boime | |
| 5,925,549 A | 7/1999 | Hsueh et al. | |
| 5,958,737 A | 9/1999 | Boime et al. | |
| 5,985,611 A | 11/1999 | Boime | |
| 6,040,157 A | 3/2000 | Hu et al. | |
| 6,103,501 A | 8/2000 | Boime et al. | |
| 6,225,449 B1 | 5/2001 | Boime | |
| 6,238,890 B1 | 5/2001 | Boime et al. | |
| 6,242,580 B1 | 6/2001 | Boime et al. | |
| 6,245,896 B1 | 6/2001 | Lee et al. | |
| 6,265,393 B1 | 7/2001 | Heinrichs | |
| 6,274,365 B1 | 8/2001 | van de Ven et al. | |
| 6,306,654 B1 | 10/2001 | Boime et al. | |
| 6,635,256 B1 | 10/2003 | Boime et al. | |
| 6,737,515 B2 | 5/2004 | Boime et al. | |
| 6,987,172 B2 | 1/2006 | Boime et al. | |
| 7,081,446 B2 * | 7/2006 | Lustbader ...................... 514/13 |
| 7,173,113 B2 | 2/2007 | Lustbader et al. | |
| 7,202,215 B2 | 4/2007 | Lustbader | |
| 7,442,684 B2 | 10/2008 | Lustbader et al. | |
| 2002/0127652 A1* | 9/2002 | Schambye et al. ........... 435/69.4 |
| 2002/0128190 A1 | 9/2002 | Lobel et al. | |
| 2003/0012792 A1 | 1/2003 | Holaday et al. | |
| 2003/0211580 A1 | 11/2003 | Lustbader | |
| 2003/0219875 A1* | 11/2003 | Rosen et al. ................ 435/69.7 |
| 2004/0258685 A1 | 12/2004 | Brunetta et al. | |
| 2005/0166274 A1 | 7/2005 | French et al. | |
| 2007/0128203 A1 | 6/2007 | Giles-Komar et al. | |
| 2008/0008650 A1 | 1/2008 | Fukuda et al. | |
| 2008/0039372 A1 | 2/2008 | Lustbader | |
| 2009/0093411 A1 | 4/2009 | Lustbader et al. | |

FOREIGN PATENT DOCUMENTS

| | | |
|---|---|---|
| EP | 0322226 | 6/1989 |
| EP | 0957167 | 11/1999 |
| WO | WO-02/072793 | 9/2002 |
| WO | WO-03/064619 | 8/2003 |
| WO | WO 03/064677 | 8/2003 |
| WO | WO-2009/052119 | 4/2009 |
| WO | WO-2010/017290 | 2/2010 |

OTHER PUBLICATIONS

Bouloux, P. M., D. J. Handelsman, F. Jockenhovel, E. Nieschlag, J. Rabinovici, W. L. Frasa, J. J. de Bie, G. Voortman, and J. Itskovitz-Eldor (2001) First human exposures to FSH-CTP in hypogonadotrophic hypogonadal males. *Hum Reprod*, 16, 1592-1597.

Calvo, F. O., H. T. Keutmann, E. R. Bergert, and R. J. Ryan (1986) Deglycosylated human follitropin: characterization and effects on adenosine cyclic 3',5'-phosphate production in porcine granulosa cells. *Biochemistry* 25, 3938-3943.

Chui, D. K., N. D. Pugh, S. M. Walker, L. Gregory, and R. W. Shaw (1997) Follicular vascularity—the predictive value of transvaginal power Doppler ultrasonography in an in vitro fertilization programme: a preliminary study. *Hum. Reprod*. 12, 191-196.

Dissen, G. A., H. E. Lara, W. H. Fahrenbach, M. E. Costa, and S. R. Ojeda (1994) Immature rat ovaries become revascularized rapidly after autotransplantation and show a gonadotropin-dependent increase in angiogenic factor gene expression. *Endocrinology* 134, 1146-1154.

Fares, F. A., N. Suganuma, K. Nishimori, P. S. Lapolt, A. J. Hsueh, and I. Boime (1992) Design of a long-acting follitropin agonist by fusing the C-terminal sequence of the chorionic gonadotropin beta subunit to the follitropin beta subunit. *Proc. Natl. Acad. Sci.* U.S.A. 89, 4304-4308.

(Continued)

*Primary Examiner*—Cecilia Tsang
*Assistant Examiner*—Thomas S Heard
(74) *Attorney, Agent, or Firm*—Wilmer Cutler Pickering Hale and Dorr LLP

(57) ABSTRACT

This invention provides FSH analogues having increased serum half-life relative to FSH. This invention also provides related compositions and methods for increasing fertility, egg production and spermatogenesis in a subject.

8 Claims, 21 Drawing Sheets

OTHER PUBLICATIONS

Feng, W., M. M. Matzuk, K. Mountjoy, E. Bedows, R. W. Ruddon, and I. Boime (1995) The asparagine-linked oligosaccharides of the human chorionic gonadotropin beta subunit facilitate correct disulfide bond pairing. *J. Biol. Chem.* 270, 11851-11859.

Ferrara, N., H. Chen, T. Davis-Smyth, H. P. Gerber, T. N. Nguyen, D. Peers, V. Chisholm, K. J. Hillan, and R. H. Schwall (1998) Vascular endothelial growth factor is essential for corpus luteum angiogenesis. *Nat. Med.* 4, 336340.

Ferrara, N., K. Houck, L. Jakeman, and D. W. Leung (1992) Molecular and biological properties of the vascular endothelial growth factor family of proteins. *Endocr. Rev.* 13, 18-32.

Krichevsky, A., S. Birken, J. F. O'Connor, K. Bikel, J. Schlatterer, and R. E. Canfield (1994) The development of a panel of monoclonal antibodies to human luteinizing hormone and its application to immunological mapping and two-site assays. *Endocrine 2*. 511-520.

LeContonnec, J. Y., H. C. Porchet, V. Beltrami, A. Khan, S. Toon, and M. Rowland (1994) Clinical pharmacology of recombinant human follicle-stimulating hormone. II. Single doses and steady-state pharmacokinetics. *Fertil. Steril.* 61, 679-86.

Lindau-Shapard, B. A., H. A. Brumberg, A. J. Peterson, and J. A. Dias (2001) Reversible immunoneutralization of human follitropin receptor. *J. Reprod. Immun.* 49, 1-19.

Matzuk, M. M., A. J. Hsueh, P. Lapolt, A. Tsafriri, J. L. Keene, and I. Boime (1990) The biological role of the carboxyl-terminal extension of human chorionic gonadotropin beta-subunit. *Endocrinology* 126, 376-383.

Nargund, G., T. Bourne, P. Doyle, J. Parsons, W. Cheng, S. Campbell, and W. Collins (1996) Associations between ultrasound indices of follicular blood flow, oocyte recovery and preimplantation embryo quality. *Hum. Reprod.* 11, 109-113.

Pedersen, T. and H. Peters (1968) Proposal for a classification of oocytes and follicles in the mouse ovary. *J. Reprod. Fertil.* 17, 555-557.

Pierce, J. G. and T. F. Parsons (1981) Glycoprotein hormones: structure and function. *Annu. Rev. Biochem.* 50, 465-495.

Porchet, H. C., J. Y. LeContonnec, B. Neuteboom, S. Canali, and G. Zanolo (1995) Pharmacokinetics of recombinant human luteinizing hormone. *J. Clin. Endocrinol. Metab.* 80, 667-73.

Saal, W., H. J. Glowania, and J. Happ (1991) Pharmacodynamics and pharmacokinetics after subcutaneous and intramuscular injection of human chorionic gonadotropin. *Fertil. Steril.* 56, 225-8.

Sairam, M. R. and P. Manjunath (1982) Studies on pituitary follitropin. XL Induction of hormonal antagonistic activity by chemical deglycosylation. *Mol. Cell Endocrinol.* 28, 139-150.

Sugahara, T., M. R. Pixley, F. Fares, and I. Boime (1996) Characterization of the O-glycosylation sites in the chorionic gonadotropin beta subunit in vivo using site-directed mutagenesis and gene transfer. *J. Biol. Chem.* 271, 20797-20804.

Suganuma, N., M. M. Matzuk, and I. Boime (1989) Elimination of disulfide bonds affects assembly and secretion of the human chorionic gonadotropin beta subunit. *J. Biol. Chem.* 264, 19302-19307.

Van Blerkom, J., M. Antczak, and R. Schrader (1997) The developmental potential of the human oocyte is related to the dissolved oxygen content of follicular fluid: association with vascular endothelial growth factor levels and perifollicular blood flow characteristics. *Hum. Reprod.* 12, 1047-1055.

Yen, S. S., O. Llerena, B. Little, and O. H. Pearson (1968) Disappearance rates of endogenous luteinizing hormone and chorionic gonadotropin in man. *J. Clin. Endocrinol. Metab.* 28, 1763-1767.

International Search Report issued Dec. 1, 2003 in connection with PCT International Application No. PCT/US03/02982 (Exhibit B).

Ben-Menahem et al. (2001) The Position of the Alpha and Beta Subunits in a Single Chain Variant of Human Chorionic Gonadotropin Affects the Heterodimeric Interaction of the Subunits and Receptor-Binding Epitope. *J. Biol. Chem.* 276:29871-879 (Exhibit C).

International Search Report issued Jan. 8, 2007 in connection with related PCT International Application No. PCT/US03/02957(Exhibit D).

Baird, D. (2001) Is there a place for different isoforms of FSH in clinical medicine? IV. The clinician's point of view, *Human Reproduction*, vol. 16, No. 6, p. 1316-1318 (Exhibit E).

Ulloa-Aguirre, et al. (2001) Endocrine Regulation of Gonadotropin Glycosylation, *Archives of Medical Research*, vol. 32, p. 520-532 (Exhibit F).

U.S. Appl. No. 10/062,910, filed Jan. 31, 2002, Joyce Lustbader et al. Advisory Action issued Oct. 6, 2005 in connection with U.S. Appl. No. 10/112,321, filed Mar. 27, 2002.

Amendment submitted Dec. 20, 2006 in connection with U.S. Appl. No. 10/357,252, filed Jan. 31, 2003.

Amendment submitted Jan. 11, 2007 in connection with U.S. Appl. No. 10/357,252, filed Jan. 31, 2003.

Amendment submitted Jul. 24, 2006 in connection with U.S. Appl. No. 10/357,252, filed Jan. 31, 2003.

Amendment submitted Jun. 24, 2005 in connection with U.S. Appl. No. 10/357,252, filed Jan. 31, 2003.

Amendment submitted Nov. 2, 2006 in connection with U.S. Appl. No. 10/357,252, filed Jan. 31, 2003.

Amendment submitted Nov. 3, 2005 in connection with U.S. Appl. No. 10/112,321, filed Mar. 27, 2002.

Amendment submitted Sep. 19, 2003 in connection with U.S. Appl. No. 10/357,252, filed Jan. 31, 2003.

Amendment submitted Sep. 6, 2005 in connection with U.S. Appl. No. 10/112,321, filed Mar. 27, 2002.

Amendment, including Exhibits A to C submitted Jan. 30, 2006 in connection with U.S. Appl. No. 10/357,252, filed Jan. 31, 2003.

Amendment, including Exhibits A to D submitted Feb. 15, 2005 in connection with U.S. Appl. No. 10/112,321, filed Mar. 27, 2002.

Amendment, including Exhibits A to E submitted Jun. 16, 2003 in connection with U.S. Appl. No. 10/357,252, filed Jan. 31, 2002.

Bishop, L.A., et al. (1995) "Both of the β-Subunit Carbohydrate Residues of Follicle-Stimulating Hormone Determine the Metabolic Clearance Rate and in Vivo Potency", Endocrinology 136(6):2635-40.

Communication submitted Oct. 21, 2004 in connection with U.S. Appl. No. 10/112,321, filed Mar. 27, 2002.

Communication submitted Oct. 7, 2005 in connection with U.S. Appl. No. 10/357,252, filed Jan. 31, 2003.

Communication, including Exhibits A and B submitted Oct. 23, 2002 in connection with U.S. Appl. No. 10/112,321, filed Mar. 27, 2002.

Communication, including Exhibits A to C submitted Apr. 17, 2003 in connection with PCT International Application No. PCT/US03/02957, filed Jan. 31, 2003.

Communication, including Exhibits A to D submitted Jul. 3, 2002 in connection with U.S. Appl. No. 10/112,321, filed Mar. 27, 2002.

Duffaud, G.D., et al. (1987) "Expression and secretion of foreign proteins in *Escherichia coli*", Methods Enzymol. 153:492-507.

Frydman, B., et al. (2000) "A double-blind, randomized study to compare recombinant human follicle stimulating hormone (FSH; Gonal-F®) with highly purified urinary FSH (Metrodin® HP) in women undergoing assisted reproductive techniques including intracytoplasmic sperm injection. The French Multicentre Trialists", Human Reprod. 15:520-525.

Gilchrist, R.B., et al. (1997) "Maturation, Fertilization, and Development of Marmoset Monkey Oocytes In Vitro", Biol. Reprod. 56:238-246.

Mikkelsen, A.L., et al. (2000) "Impact of oestradiol and inhibin A concentrations on pregnancy rate in in-vitro oocyte maturation", Human Reprod. 15:1685-1690.

Ng, E.H.Y., et al. (2001) "HMG is as good as recombinant human FSH in terms of oocyte and embryo quality: a prospective randomized trial", Human Reprod. 16:319-325.

Office Action issued Apr. 24, 2006 in connection with U.S. Appl. No. 10/357,252, filed Jan. 31, 2003.

Office Action issued Jun. 2, 2005 in connection with U.S. Appl. No. 10/357,252, filed Jan. 31, 2003.

Office Action issued Jun. 3, 2005 in connection with U.S. Appl. No. 10/112,321, filed Mar. 27, 2002.

Office Action issued Nov. 15, 2004 in connection with U.S. Appl. No. 10/112,321, filed Mar. 27, 2002.

Office Action issued Sep. 21, 2004 in connection with U.S. Appl. No. 10/112,321, filed Mar. 27, 2002.

Office Action issued Sep. 7, 2005 in connection with U.S. Appl. No. 10/357,252, filed Jan. 31, 2003.

Out, H.J., et al. (2000) "Increasing the daily dose of recombinant follicle stimulating hormone (Puregon®) does not compensate for the age-related decline in retrievable oocytes after ovarian stimulation", Human Reprod. 15:29-35.

Preliminary Amendment submitted Jan. 31, 2002 in connection with U.S. Appl. No. 10/062,910, filed Jan. 31, 2002.

Preliminary Amendment submitted Jan. 31, 2003 in connection with U.S. Appl. No. 10/357,252, filed Jan. 31, 2003.

Preliminary Amendment submitted Mar. 27, 2002 in connection with U.S. Appl. No. 10/112,321, filed Mar. 27, 2002.

Second Communication, including Exhibits A to C submitted Apr. 17, 2003 in connection with PCT International Application No. PCT/US03/02957, filed Jan. 31, 2003.

Wynn, P., et al. (1998) "Pretreatment with follicle stimulating hormone promotes the numbers of human oocytes reaching metaphase II by in-vitro maturation", Human Reprod. 13:3132-3138.

Yeoman, R.R., et al. (1994) "Restoration of Oocyte Maturational Competency during the Nonbreeding Season with Follicle-Stimulating Hormone Stimulation in Squirrel Monkeys (*Saimiri boliviensis boliviensis*)", Biol. Reprod. 50:329-335.

Available to the Examiner on PAIR.

Issued Oct. 6, 2005 in connection with U.S. Appl. No. 10/112,321, filed Mar. 27, 2002.

Submitted Dec. 20, 2006 in connection with U.S. Appl. No. 10/357,252, filed Jan. 31, 2003.

Submitted Jan. 11, 2007 in connection with U.S. Appl. No. 10/357,252, filed Jan. 31, 2003.

Submitted Jul. 24, 2006 in connection with U.S. Appl. No. 10/357,252, filed Jan. 31, 2003.

Submitted Jun. 24, 2005 in connection with U.S. Appl. No. 10/357,252, filed Jan. 31, 2003.

Submitted Nov. 2, 2006 in connection with U.S. Appl. No. 10/357,252, filed Jan. 31, 2003.

Submitted Nov. 3, 2005 in connection with U.S. Appl. No. 10/112,321, filed Mar. 27, 2002.

Submitted Sep. 19, 2003 in connection with U.S. Appl. No. 10/357,252, filed Jan. 31, 2003.

Submitted Sep. 6, 2005 in connection with U.S. Appl. No. 10/112,321, filed Mar. 27, 2002.

Submitted Jan. 30, 2006 in connection with U.S. Appl. No. 10/357,252, filed Jan. 31, 2003.

Submitted Feb. 15, 2005 in connection with U.S. Appl. No. 10/112,321, filed Mar. 27, 2002.

Submitted Jun. 16, 2003 in connection with U.S. Appl. No. 10/357,252, filed Jan. 31, 2003.

Cited in an Jun. 3, 2005 Office Action issued in connection with U.S. Appl. No. 10/112,321, filed Mar. 27, 2002.

Submitted Oct. 21, 2004 in connection with U.S. Appl. No. 10/112,321, filed Mar. 27, 2002.

Submitted Oct. 7, 2005 in connection with U.S. Appl. No. 10/357,252, filed Jan. 31, 2003.

Submitted Oct. 23, 2002 in connection with U.S. Appl. No. 10/112,321, filed Mar. 27, 2002.

Included herewith as Exhibit 1.

Submitted Jul. 3, 2002 in connection with U.S. Appl. No. 10/112,321, filed Mar. 27, 2002.

Cited in an Jun. 3, 2005 Office Action issued in connection with U.S. Appl. No. 10/112,321, filed Mar. 27, 2002.

Cited in an Apr. 24, 2006 Office Action issued in connection with U.S. Appl. No. 10/357,252, filed Jan. 31, 2003.

Cited in an Apr. 24, 2006 Office Action issued in connection with U.S. Appl. No. 10/357,252, filed Jan. 31, 2003.

Cited in an Apr. 24, 2006 Office Action issued in connection with U.S. Appl. No. 10/357,252, filed Jan. 31, 2003.

Cited in an Apr. 24, 2006 Office Action issued in connection with U.S. Appl. No. 10/357,252, filed Jan. 31, 2003.

Issued Apr. 24, 2006 in connection with U.S. Appl. No. 10/357,252, filed Jan. 31, 2003.

Issued Jun. 2, 2005 in connection with U.S. Appl. No. 10/357,252, filed Jan. 31, 2003.

Issued Jun. 3, 2005 in connection with U.S. Appl. No. 10/112,321, filed Mar. 27, 2002.

Issued Nov. 15, 2004 in connection with U.S. Appl. No. 10/112,321, filed Mar. 27, 2002.

Issued Sep. 21, 2004 in connection with U.S. Appl. No. 10/112,321, filed Mar. 27, 2002.

Issued Sep. 7, 2005 in connection with U.S. Appl. No. 10/357,252, filed Jan. 31, 2003.

Cited in an Apr. 24, 2006 Office Action issued in connection with U.S. Appl. No. 10/357,252, filed Jan. 31, 2003.

Submitted Jan. 31, 2002 in connection with U.S. Appl. No. 10/062,910, filed Jan. 31, 2002.

Submitted Jan. 31, 2003 in connection with U.S. Appl. No. 10/357,252, filed Jan. 31, 2003.

Submitted Mar. 27, 2002 in connection with U.S. Appl. No. 10/112,321, filed Mar. 27, 2002.

Included herewith as Exhibit 2.

Cited in an Apr. 24, 2006 Office Action issued in connection with U.S. Appl. No. 10/357,252, filed Jan. 31, 2003.

Cited in an Apr. 24, 2006 Office Action issued in connection with U.S. Appl. No. 10/357,252, filed Jan. 31, 2003.

U.S. Appl. No. 10/062,931, Joyce Lustbader et al.

A. Revelli, et al., "Recombinant versus highly-purified, urinary follicle-stimulating hormone (r-FSH vs. HP-uFSH) in ovulation induction: a prospective, randomized study with cost-minimization analysis," (2006) Reprod Biol Endocrinol 4:38.

Abdalla et al., "The effect of the dose of human chorionic gonadotropin and the type of gonadotropin stimulation on oocyte receovery rates in an in vitro fertilization program," Fertil Steril 48:958-963 (1987).

Alam H, et al, Follicle stimulating hormone activation of hypoxia inducible factor 1 by the phosphatidylinositol 3 kinase/AKT/Ras homolog enriched in brain (Rheb)/mammalian target of rapamycin (mTOR) pathway is necessary for induction of select protein markers of follicular differentiation. J Biol Chem 279:19431-19440 (2004).

Amso et al., "The management of predicted ovarian hyperstimulation involving gonadotropin-releasing hormone analog with elective cryopreservation of all pre-embryos," Fertil Steril 53, 1087-1090 (1990).

Arockiasamy A, et al., (1999), "Crystallization of the immunodominant outer membrane protein OmpC; the first protein crystals from *Salmonella typhi*, a human pathogen," FEBS Lett 453:380-382.

Arora et al., "Vascular Endothelial Growth Factor Chimeric Toxin Is Highly Active against Endothelial Cells," Cancer Res., vol. 59, pp. 183-188 (1999).

Ascoli et al., "On the structure of the luteinizing hormone/chorionic gonadotropin receptor. [Review]," Endocrine Reviews 10:27-44 (1989).

Auranen A, et al., (2005), "Hormonal treatments and epithelial ovarian cancer risk," Int J Gynecol Cancer 15:692-700.

Backer et al., "Functionally Active VEGF Fusion Proteins," Protein Expression and Purification, vol. 23, pp. 1-7 (2001).

Ben Josef et al., "Hormone-refractory prostate cancer cells express functional follicle-stimulating hormone receptor (FSHR)," J Urol 161:970-976 (1999).

Bernard et al., "Lutropins appear to contact two independent sites in the extracellular domain of their receptors," Biochem J 335 (Pt 3):611-617 (1998).

Bhalla et al., "Demonstration of hCG binding sites and hCG stimulated steroidogenesis in different populations of interstitial cells," Adv Exp Med Biol 219:489-513 (1987).

Bielinska M, et al., (1989), "Site specific processing of the N linked oligosaccharides of the human chorionic gonadotropin alpha subunit," J Biol Chem 264:17113-17118.

Birken S, et al., (1986) "Tryptic digestion of the alpha subunit of human choriogonadotropin," J Biol Chem 261:10719-10727.

Biskind GR, et al.,(1953), "The effect of exogenous gonadotrophins on the development of experimental ovarian tumors in rats," Cancer Res 13:216-220.

Blithe et al., "Free alpha molecules from pregnancy stimulate secretion of prolactin from human decidual cells: a novel function for free alpha in pregnancy," Endocrinology 129:2257-2259 (1991).

Bonfrer et al., "Technical evaluation of three second generation CA 125 assays," Eur J Clin Chem Clin Biochem 32:201-207 (1994).
Bongso et al., "Human embryonic behavior in a sequential human oviduct-endometrial coculture system," Fertility & Sterility 61:976-978 (1994).
Bonnamy et al., "Uterine luteinizing hormone/human chorionic gonadotropin-binding sites in the early pregnant rat uterus: evidence for total occupancy in the periimplantation period," Endocrinology 132:1240-1246 (1993).
Bosl GJ, et al. (1997), "Testicular germ cell cancer.," N Engl J Med 337:242-253.
Bosl GJ, et al., (1981) "Tumor markers in advanced nonseminomatous testicular cancer," Cancer 47:572-576.
Braun et al., "Amino-terminal leucine-rich repeats in gonadotropin receptors determine hormone selectivity," EMBO Journal 10:1885-1890 (1991).
Butters et al., "Effects of N-butyldeoxynojirmycin and the Lec3.2.8.1 mutant phenotype on N-glycan processing in Chinese hamster ovary cells: application to glycoprotein crystallization," Protein Sci. 8, 1696-1701 (1999).
Campbell et al., "Conversion of human choriogonadotropin into a follitropin by protein engineering," Proc Natl Acad Sci U S A 88:760-764 (1991).
Carson et al., "The c-kit ligand suppresses apoptosis of human natural killer cells through the upregulation of bcl-2," Proc Natl Acad Sci U S A 91:7553-7557 (1994).
Carter CW, et al., (1979), "Protein crystallization using incomplete factorial experiments," Journal of Biological Chemistry 254:12219-12223.
Chakravarti S, et al., (1979), "Relation between plasma hormone profiles, symptoms, and response to oestrogen treatment in women approaching the menopause," Br Med J 1:983-985.
Channing CP, et al., (1978) "Role of the carbohydrate residues of human chorionic gonadotropin in binding and stimulation of adenosine 3',5' monophosphate accumulation by porcine granulosa cells," Endocrinology 103:341-348.
Charlesworth et al., "Inhibition of human choriotropin binding to receptor by human choriotropin alpha peptides. A comprehensive synthetic approach," Journal of Biological Chemistry 262:13409-13416 (1987).
Chatzaki et al., "Characterisation of the differential expression of marker antigens by normal and malignant endometrial epithelium," British Journal of Cancer 69:1010-1014 (1994).
Chen et al., "High expression of the hormone binding active extracellular domain (1-294) of rat lutropin receptor in *Escherichia coli*. Molecular & Cellular," Endocrinology 91:35-41 (1993).
Chen et al., "Characterization and biological properties of Chemically Deglycosylated Human Chorionic Gonadotropin," J Biol Chem 257, pp. 14446-14452 (1982).
Choi JH et al., (2004) "Overexpression of follicle stimulating hormone receptor activates oncogenic pathways in preneoplastic ovarian surface epithelial cells," J Clin Endocrinol Metab 89:5508-5516.
Choi JH, et al.(2007)"Gonadotropins and ovarian cancer," Endocr Rev 28:440-461.
Choi JH, et al., (2006) "Differential regulation of two forms of gonadotropin releasing hormone messenger ribonucleic acid by gonadotropins in human immortalized ovarian surface epithelium and ovarian cancer cells," Endocr Relat Cancer 13:641-651.
Chothia et al., "The relation between the divergence of sequence and structure in proteins," EMBO Journal 5:823-826 (1986).
Christin-Maitre et al., "Homologous in vitro bioassay for Foolicle-Stimulating Hormone (FSH) reveals increased FSH Biological Signal during the Mid-to late luteal phase of the Human Menstrual cycle," (1996) JCEM 81(6); pp. 2080-2088.
Christin-Maitre, "Bioassays of gonadotropins based on cloned receptors," (1996) Mol Cell Endo 125, 151-159.
Cleveland DW, (1977) "Peptide mapping by limited proteolysis in sodium dodecyl sulfate and analysis by gel electrophoresis," Journal of Biological Chemistry 252:1102-1106.
Cole et al., "Detecting and Monitoring Trophoblastic Disease. New perspectives on Measuring Human Chorionic Gonadotropin Levels," J Reprod Med 39.193-200, (1994).

Cole et al., "Urine hCG β-Subunit Core Fragment, a Sensitive Test for Ectopic Pregnancy," J Clin Endocrinol Metab 78:497-499 (1994).
Cole LA, et al., (2006) "Gestational trophoblastic diseases: 1. Pathophysiology of hyperglycosylated hCG," Gynecol Oncol 102:145-150.
Cramer DW, et al., (1983) "Determinants of ovarian cancer risk. I. Reproductive experiences and family history," J Natl Cancer Inst 71:711-716.
Cramer DW, et al., (1983) "Determinants of ovarian cancer risk. II. Inferences regarding pathogenesis," J Natl Cancer Inst 71:717-721.
Crotzer DR, et al., (2007) "Lack of effective systemic therapy for recurrent clear cell carcinoma of the ovary," Gynecol Oncol 105:404-408.
Das et al., "Heparin-binding EGF-like growth factor gene is induced in the mouse uterus temporally by the blastocyst solely at the site of its apposition: a possible ligand for interaction with blastocyst EGF-receptor in implantation," Development 120:1071-1083 (1994).
Davies A, et al., (1996) "Projection structure of an invertebrate rhodopsin," J Struct Biol 117:36-44.
Derman et al., "Mutations that allow disulfide bond formation in the cytoplasm of *Escherichia coli*," Science 262:1744-1747 (1993).
Dias JA, et al., (2001) "Structural biology of human follitropin and its receptor," Arch Med Res 32:510-519.
Dimitriadou et al., "Discordant secretion of pregnancy specific beta 1-glycoprotein and human chorionic gonadotropin by human pre-embryos cultured in vitro," Fertility & Sterility 57:631-636 (1992).
Dokras et al., "Human blastocyst grading: an indicator of developmental potential?," Human Reproduction 8:2119-2127 (1993).
Dokras et al., "Human trophectoderm biopsy and secretion of chorionic gonadotrophin," Human Reproduction 6:1453-1459 (1991).
Dokras et al., "The human blastocyst: morphology and human chorionic gonadotrophin secretion in vitro," Human Reproduction 6:1143-1151 (1991).
Dolbeare et al., "Using monoclonal antibodies in bromodeoxyuridine-DNA analysis," Methods Cell Biol 33:207-216 (1990).
Droz JP, et al. (1988) "Prognostic factors in advanced nonseminomatous testicular cancer. A multivariate logistic regression analysis," Cancer 62:564-568.
Dufau et al., "Purification and characterization of ovarian Lh/hCG and prolactin receptors," Journal of Receptor Research 7:167-193 (1987).
Dufau ML, "The luteinizing hormone receptor," Annu Rev Physiol 60:461-496 (1998).
Dunaif A (2006), "Insulin resistance in women with polycystic ovary syndrome," Fertil Steril 86 Suppl 1:S13-14.
Edwards RG, "Implantation, interception and contraception," Human Reproduction 9:985-995 (1994).
Einhorn LH, et al., (1981) "The role of maintenance therapy in disseminated testicular cancer.," N Engl J Med 305:727-731.
Fares FA, et al., (1996) "The role of the asparagine linked oligosaccharides of the alpha subunit in human thyrotropin bioactivity," Endocrinology 137:555-560.
Frederick et al., "Successful pregnancy outcome after cryopreservation of all fresh embryos with subsequent transfer into an unstimulated cycle," Fertil Steril 64, 987-990 (1995).
Fernandez et al., "Identification of amino acid residues in transmembrane helices VI and VII of the lutropin/choriogonadotropin receptor involved in signaling," Biochemistry 35:3986-3993 (1996).
Fernandez et al., "Lys583 in the Third Extracellular Loop of the Lutropin/Choriogonadotropin Receptor is critical for Signaling," Journ. of Biolog. Chem. vol. 271, pp. 925-930 (1996).
Fiddes et al., "The cDNA for β-subunit of human chorionic gonadotropin suggest evolution of a gene by readthrough into the 3'-untranslanted region," Nature 286(5774):684-7 (1980).
Funahashi Y, et al., (2002) "Sulfonamide derivative, E7820, is a unique angiogenesis inhibitor suppressing an expression of integrin alpha2 subunit on endothelium," Cancer Res 62:6116-6123.
Gabrilovich et al., Chapter 44 in the Cytokine Handbook, 4th Edition. Ed: Thomson et al. Academic Press, pp. 1017-1034 (2003).

Gachhui et al., "Characterization of the reductase domain of rat neuronal nitric oxide synthase generated in the methylotrophic yeast *Pichia pastoris*. Calmodulin response is complete within the reductase domain itself," Journal of Biological Chemistry 271:20594-20602 (1996).

Gadducci A, et al., (2004) "Sex steroid hormones, gonadotropin and ovarian carcinogenesis: a review of epidemiological and experimental data," Gynecol Endocrinol 19:216-228.

Ganelin C, "Past approaches to discovering new drugs," In: Wermuth C (ed). Medicinal Chemistry for the 21st Century.Blackwell Oxford,3-12 (1992).

Gels ME,et al (1995) "Detection of recurrence in patients with clinical stage I nonseminomatous testicular germ cell tumors and consequences for further follow up: a single center 10 year experience," J Clin Oncol 13:1188-1194.

Gersak B, et al., (2002), "Right ventricular metastatic choriocarcinoma obstructing inflow and outflow tract," Ann Thorac Surg 73:1631-1633.

Gompel A, Sabourin JC, Martin A, Yaneva H, Audouin J, Decroix Y, Poitout P, "Bcl-2 expression in normal endometrium during the menstrual cycle," Am J Pathol 144: pp. 1195-1202 (1994).

Gouaux E, et al, (1997), "alpha-Hemolysin, gamma-hemolysin, and leukocidin from *Staphylococcus aureus*: distant in sequence but similar in structure," Protein Science 6:2631-2635.

Gouaux JE, et al., (1994), "Subunit stoichiometry of staphylococcal alpha-hemolysin in crystals and on membranes: a heptameric transmembrane pore," Proc Natl Acad Sci U S A 91:12828-12831.

Graf et al., "Decreased spermatogenesis as the result of an induced autoimmune reaction directed against the gonadotropin receptors in male rats," J Androl 18:174-185 (1997).

Gray et al., "Cell cycle analysis using flow cytometry," Int J Radiat Biol Relat Stud Phys Chem Med 49:237-255 (1986).

Greer JB, et al., (2005), "Short term oral contraceptive use and the risk of epithelial ovarian cancer," Am J Epidemiol 162:66-72.

Grossmann M, et al., (1997), "Human thyroid stimulating hormone (hTSH) subunit gene fusion produces hTSH with increased stability and serum half life and compensates for mutagenesis induced defects in subunit association," J Biol Chem 272:21312-21316.

Guderman et al., "In vitro Bioassay for Human Serum Follicle-Stimulating Hormone (FSH) Based on L cells Transfected with Recombinant Rat FSH Receptor: Validation of a Model System," (1994) Endocrinology, vol. 135, pp. 2204-2213.

Gunn et al., "Lack of evidence for the production of interferon-alpha-like species by the cultured human pre-embryo," Human Reproduction 9:1522-1527 (1994).

Halin et al., "Tumor-Targeting Properties of Antibody-Vascular Endothelial Growth Factor Fusion Proteins," Int. J. Cancer, vol. 102, pp. 109-116 (2002).

Hamilton TC, et al., (1983), "Characterization of a human ovarian carcinoma cell line (NIH:OVCAR3) with androgen and estrogen receptors," Cancer Res 43:5379-5389.

Hansen et al, "Re-examination and further development of a precise and rapid dye method for measuring cell growth/cell kill," Journal of Immunological Methods 119:203-210 (1989).

Harikumar R, et al., (2004), "Testicular choriocarcinoma with gastric metastasis presenting as hematemesis," Indian J Gastroenterol 23:223-224.

Hay et al., "Chorionic gonadotropin secretion by human embryos in vitro," J Clin Endocrinol Metab 67:1322-1324 (1988).

Hendrickson WA, et al., (1990), "Selenomethionyl proteins produced for analysis by multiwavelength anomalous diffraction (MAD): a vehicle for direct determination of three-dimensional structure," EMBO Journal 9:1665-1672.

Hirsch A, et al., (1995), "Purification, characterization, crystallization, and preliminary X-ray results from *Paracoccus denitrificans porin*," Proteins 23:282-284.

Hoff et al., "Hormonal Dynamics at Midcycle: A reevaluation," J Clin Endocrinol Metab 57:892-896 (1983).

Hong et al., "The alpha-subunit of human choriogonadotropin interacts with the exodomain of the luteinizing hormone/choriogonadotropin receptor," Endocrinology 140:2486-2493 (1999).

Hong et al., "The amino-terminal region of the luteinizing hormone/choriogonadotropin receptor contacts both subunits of human choriogonadotropin," I. Mutational analysis. J Biol Chem 273:13835-13840 (1998).

Hong et al., "The beta-subunit of human choriogonadotropin interacts with the exodomain of the luteinizing hormone/choriogonadotropin receptor and changes its interaction with the alpha-subunit," Mol Endocrinol 13:1285-1294 (1999).

Hortin G, et al., (1980), "Inhibition of asparagine linked glycosylation by incorporation of a threonine analog into nascent peptide chains," J Biol Chem 255:8007-8010.

Horvat B, "Galactose-binding lectins as markers of pregnancy-related glycoproteins," Histochemistry 99:95-101 (1993).

Huang CF et al, (2003), "Follicle stimulating hormone inhibits cisplatin induced apoptosis in ovarian cancer cells," Zhongguo Yi Xue Ke Xue Yuan Xue Bao 25:447-450.

Huang et al., "Effects of gonadotropin on steroidogenesis by luteinized human granulosa cells," J Formos Med Assoc 92:618-622 (1993).

Hustin et al., "Immunohistochemical localization of two endometrial proteins in the early days of human pregnancy," Placenta 15:701-708 (1994).

Ibanez L, et al., (1996), "Ovarian 17 hydroxyprogesterone hyper-responsiveness to gonadotropin releasing hormone (GnRH) agonist challenge in women with polycystic ovary syndrome is not mediated by luteinizing hormone hypersecretion: evidence from GnRH agonist and human chorionic gonadotropin stimulation testing," J Clin Endocrinol Metab 81:4103-4107.

Ikura et al., "A novel approach for sequential assignment of 1H, 13C, and 15N spectra of proteins: heteronuclear triple-resonance three-dimensional NMR spectroscopy," Application to calmodulin. Biochemistry 29:4659-4667 (1990).

Iles et al., Expression of beta human chorionic gonadotrophin by non-trophoblastic non-endocrine 'normal' and malignant epithelial cells. British Journal of Cancer 61:663-666 (1990).

Iles et al., Immunochemical analysis of the human chorionic gonadotrophin-like material secreted by 'normal' and neoplastic urothelial cells, J Mol Endocrinol 2:107-112 (1989).

Iles RK, (2007) "Ectopic hCGbeta expression by epithelial cancer: malignant behaviour, metastasis and inhibition of tumor cell apoptosis," Mol Cell Endocrinol 260-262:264-270.

Ilesanmi et al., "Immunohistochemical markers of uterine receptivity in the human endometrium," Microsc Res Tech 25:208-222 (1993).

Itskovitz et al., "Induction of preovulatory luteinizing hormone surge and prevention of ovarian hyperstimulation syndrome by gonadotropin-releasing hormone agonist," Fertil Steril, 56:213-220 (1991).

Jaffe EA, et al., (1973), "Culture of human endothelial cells derived from umbilical veins. Identification by morphologic and immuno-logic criteria," J Clin Invest 52:2745-2756.

Jeoung et al., "Hormone Interactions to Leu Rich Repeats in the Gonadotropin Receptors: III. Photoaffinity labeling of Human Chorionic Gonadotropin with Receptor Leu Rich Repeat 4 Peptide," Journal of Biological Chemistry, vol. 276, pp. 3443-3450 (2000).

Ji et al., "Macromolecular photoaffinity labeling of the lutropin receptor on granulosa cells," Proc Natl Acad Sci U S A 77:7167-7170 (1980).

Ji et al., "Presence of spectrin tetramer on the erythrocyte membrane," Journal of Biological Chemistry 255:2990-2993 (1980).

Ji et al., "Differential roles of exoloop 1 of the human follicle-stimulating hormone receptor in hormone binding and receptor activation," Journal of Biological Chemistry 270:15970-15973 (1995).

Ji et al., "Receptor activation is distinct from hormone binding in intact lutropin-choriogonadotropin receptors and Asp397 is important for receptor activation," J Biol Chem 268:20851-20854 (1993).

Jia et al., "Expression of human luteinizing hormone (LH) receptor: interaction with LH and chorionic gonadotropin from human but not equine, rat, and ovine species," Molecular Endocrinology 91:759-768 (1991).

Jia, XC, et al., "Serum Bioactive follicle-Stimulating Hormone during the human Menstrual cycle and in Hyper- and hypogonadotropic States: Application of a senitive granulosa cell aromatase bioassay," J Clin Endocrinol Metab. (Jun. 1986);62(6): 1243-1249.

Kalyan NK, et al., (1983), "Role of carbohydrate in human chorionic gonadotropin. Effect of deglycosylation on the subunit interaction and on its in vitro and in vivo biological properties," J Biol Chem 258:67-74.

Kanakas N, et al., (2006), "Fertility drugs and gynecologic cancer," Ann N Y Acad Sci 1092:265-278.

Keene JL, et al., (1989), "Expression of recombinant human choriogonadotropin in Chinese hamster ovary glycosylation mutants," Mol Endocrinol 3:2011-2017.

Keene JL, et al., (1994), "Recombinant deglycosylated human FSH is an antagonist of human FSH action in cultured rat granulosa cells," Endocr J 2:175-178.

Keller G, et al., (2005), "Human malignant melanomas express receptors for luteinizing hormone releasing hormone allowing targeted therapy with cytotoxic luteinizing hormone releasing hormone analogue," Cancer Res 65:5857-5863.

Kelton,CA, et al, "The cloning of the human follicle stimulating hormone receptor and its expression in COS-7, CHO, and Y-1 cells," Mol Cell Endocrinol 1992, 89 141-151.

Kessler et al., "Structures of N-Glycosidic Carbohydrate Units of human Chorionic Gonadotropin," J. Biol. Chem 254, 7901-7908 (1979).

Keutmann HT, et al., (1983), "Chemically deglycosylated human chorionic gonadotropin subunits: characterization and biological properties," Biochemistry 22:3067-3072.

Klein J, et al., (2003), "Development and characterization of a long acting recombinant hFSH agonist," Human Reprod 18:50-56.

Kornyei et al., "Human myometrial smooth muscle cells are novel targets of direct regulation by human chorionic gonadotropin," Biology of Reproduction 49:1149-1157 (1993).

Kudo M, Osuga Y, Kobilka BK, Hsueh AJW, Transmembrane regions V and VI of the human luteinizing hormone receptor are required for constitutive activation by a mutation in the third intracellular loop. Journal of Biological Chemistry 271:22470-22478 (1996).

Kumar S, Talwar GP, Biswas DK, Necrosis and inhibition of growth of human lung tumor by anti-alpha-human chorionic gonadotropin antibody. J Natl Cancer Inst 84:42-47 (1992).

Kumar TR, et al., (1995), "Transgenic mouse models for tumour suppressor genes," J Intern Med 238:233-238.

Kumar TR, et al., (1996), "Gonadotropins are essential modifier factors for gonadal tumor development in inhibin deficient mice," Endocrinology 137:4210-4216.

Kumar TR, et al., (1999) "Transgenic models to study gonadotropin function: the role of follicle stimulating hormone in gonadal growth and tumorigenesis," Mol Endocrinol 13:851-865.

Kwong PD, et al., (1999), "Probability analysis of variational crystallization and its application to gp120, the exterior envelope glycoprotein of type 1 human immunodeficiency virus (HIV-1)," Journal of Biological Chemistry 274:4115-4123.

Laemmli UK ,(1970), "Cleavage of structural proteins during the assembly of the head of bacteriophage T4," Nature 70:680-685.

Laemmli UK, et al., (1973), "Maturation of the head of bacteriophage T4. I. DNA packaging events," Journal of Molecular Biology 73:575-599.

Lange PH, et al., (1982), "Marker half life analysis as a prognostic tool in testicular cancer," J Urol 128:708-711.

Lapthorn AJ, Harris DC, Littlejohn A, Lustbader JW, Canfield RE, Machin KJ, Morgan FJ, Isaacs NW, Crystal structure of human chorionic gonadotropin [see comments]. Nature 369:455-461 (1994).

Leahy DJ, et al., (1994), "Crystallization of a fragment of human fibronectin: introduction of methionine by site-directed mutagenesis to allow phasing via selenomethionine," Proteins 19:48-54.

Lee (1990) Fertil Steril 53.

Lee "Human Folliculat Fluid contains a Follicle-Stimulating Hormone (FSH) Receptor Binding inhibitor which has FSH Agonist Activity, is Immunologically Similar to FSH, but can be distinguished from FSH," (1991) JCEM 72:1102-1107.

Lee DW, "Purification of a High Molecular Weight Follicle-Stimulating Hormone Receptor-Binding Inhibitor from Human Follicular Fluid," (1993) J Clin Endo Met 77.

Lei ZM, et al., (1992), "The expression of human chorionic gonadotropin/human luteinizing hormone receptors in human gestational trophoblastic neoplasms," J Clin Endocrinol Metab 74:1236-1241.

Lei ZM, Toth P, Rao CV, Pridham D, Novel coexpression of human chorionic gonadotropin (hCG)/human luteinizing hormone receptors and their ligand hCG in human fallopian tubes. J Clin Endocrinol Metab 77:863-872 (1993).

Licht P, Cao H, Zuo J, Lei ZM, Rao V, Merz WE, Day TG, Lack of self-regulation of human chorionic gonadotropin biosynthesis in human choriocarcinoma cells. J Clin Endocrinol Metab 78:1188-1194 (1994).

Lincoln SR, Lei ZM, Rao CV, Yussman MA, The expression of human chorionic gonadotropin/human luteinizing hormone receptors in ectopic human endometrial implants. J Clin Endocrinol Metab 75:1140-1144 (1992).

Liu X, DePasquale JA, Griswold MD, Dias JA, Accessibility of rat and human follitropin receptor primary sequence (R265-S296) in situ. Endocrinology 135:682-691 (1994).

Lobel L, Pollak S, Wang S, Chaney M, Lustbader JW, Expression and characterization of recombinant beta-subunit hCG homodimer. Endocrine 10:261-270 (1999).

Lobel Li, Pollak S, Klein J, Lustbader JW, High-Level Bacterial Expression of a Natively Folded, Soluble Extracellular Domain Fusion Protein of the Human Luteinizing Hormone/Chorionic Gonadotropin Receptor in the Cytoplasm of Escherichia coli. Endocrine 14, pp. 205-212 (2001).

Lobel Li, Rausch P, Trakht I, Pollak S, Lustbader JW, Filamentous phage displaying the extracellular domain of the hLH/CG receptor bind hCG specifically. Endocrinology 138:1232-1239 (1997).

Lojun S, Bao S, Lei ZM, Rao CV, Presence of functional luteinizing hormone/chorionic gonadotropin (hCG) receptors in human breast cell lines: implications supporting the premise that hCG protects women against breast cancer. Biology of Reproduction 57:1202-1210 (1997).

Lopata a, Hay DL, The potential of early human embryos to form blastocysts, hatch from their zona and secrete HCG in culture. Human Reproduction 4:87-94 (1989).

Lustbader JW, Birken S, Pileggi NF, Kolks MA, Pollak S, Cuff ME, Yang W, Hendrickson WA, Canfield RE, Crystallization and characterization of human chorionic gonadotropin in chemically deglycosylated and enzymatically desialylated states. Biochemistry 28:9239-9243 (1989).

Lustbader JW, Wu H, Birken S, Pollak S, Gawinowicz Kolks MA, Pound AM, Austen D, Hendrickson WA, Canfield RE, The expression, characterization, and crystallization of wild-type and selenomethionyl human chorionic gonadotropin. Endocrinology 136:640-650 (1995).

Lustbader JW, Yarmush DL, Birken S, Puett D, Canfield RE, "The application of chemical studies of human chorionic gonadotropin to visualize its three-dimensional structure. [Review]," Endocrine Reviews 14:291-311 (1993).

Marcillac I, Troalen F, Bidart JM, Ghillani P, Ribrag V, Escudier B, Malassagne B, Droz JP, Lhomme C, Rougier P, Free human chorionic gonadotropin beta subunit in gonadal and nongonadal neoplasms. Cancer Research 52:3901-3907 (1992).

Mathialagan N, Roberts RM, A role for cytokines in early pregnancy. Indian J Physiol Pharmacol 38:153-162 (1994).

Matthews CH, et al., (1993), "Primary amenorrhoea and infertility due to a mutation in the β-subunit of follicle-stimulating hormone," Nat Genet 5:81-86.

Matzuk et al., "Site Specification of the Chorionic Gonadotropin N-Linked Oligosaccharides in Signal transduction," J Biol Chem 264, 2409-2414 (1989).

Matzuk MM, et al, (1987), "Effects of preventing O glycosylation on the secretion of human chorionic gonadotropin in Chinese hamster ovary cells," Proc Natl Acad Sci U S A 84:6354-6358.

Matzuk MM, et al., (1988), "Site specific mutagenesis defines the intracellular role of the asparagine linked oligosaccharides of chorionic gonadotropin beta subunit," J Biol Chem 263:17106-17111.

Matzuk MM, et al., (1988), "The role of the asparagine linked oligosaccharides of the alpha subunit in the secretion and assembly of human chorionic gonadotrophin," J Cell Biol 106:1049-1059.

Matzuk MM, et al., (2003), "Overexpression of human chorionic gonadotropin causes multiple reproductive defects in transgenic mice," Biol Reprod 69:338-346.

McCarthy NJ, Smith CA, Williams Gt, Apoptosis in the development of the immune system: growth factors, clonal selection and bcl-2. Cancer Metastasis Rev 11:157-178 (1992).

McPherson A, Koszelak S, Axelrod H, Day J, Williams R, Robinson L, McGrath M, Cascio D, An experiment regarding crystallization of soluble proteins in the presence of beta-octyl glucoside. Journal of Biological Chemistry 261:1969-1975 (1986).

Meduri G, Charnaux N, Loosfelt H, Jolivet A, Spyratos F, Brailly S, Milgrom E, Luteinizing hormone/human chorionic gonadotropin receptors in breast cancer. Cancer Research 57:857-864 (1997).

Mellor SJ, Thomas EJ, The actions of estradiol and epidermal growth factor in endometrial and endometriotic stroma in vitro. Fertility & Sterility 62:507-513 (1994).

Minegishi T, Igarashi S, Nakamura K, Nakamura M, Tano M, Shinozaki H, Miyamoto K, Ibuki Y, Functional expression of the recombinant human FSH receptor. Journal of Endocrinology 141:369-375 (1994).

Morbeck DE, Roche PC, Keutmann HT, McCormick DJ, A receptor binding site identified in the region 81-95 of the beta-subunit of human luteinizing hormone (LH) and chorionic gonadotropin (hCG). Molecular & Cellular Endocrinology 97:173-181 (1993).

Mosgaard BJ, et al., (1997), "Infertility, fertility drugs, and invasive ovarian cancer: a case control study," Fertil Steril 67:1005-1012.

Mosgaard BJ, et al., (1998), "Ovarian stimulation and borderline ovarian tumors: a case control study," Fertil Steril 70:1049-1055.

Mosmann T, Rapid colorimetric assay for cellular growth and survival: application to proliferation and cytotoxicity assays. Journal of Immunological Methods 65:55-63 (1983).

Moyle et al., "Role of the Carbohydrate of Human Chorionic Gonadotropin in the Mechamism of Hormone Action," J Biol Chem 250, 9163-9169 (1975).

Moyle WR, Campbell RK, Myers RV, Bernard MP, Han Y, Wang X, Co-evolution of ligand-receptor pairs. Nature 368:251-255 (1994).

Moyle WR, Campbell RK, Rao SN, Ayad NG, Bernard MP, Han Y, Wang Y, Model of human chorionic gonadotropin and lutropin receptor interaction that explains signal transduction of the glycoprotein hormones. Journal of Biological Chemistry 270:20020-20031 (1995).

Moyle WR, Ehrlich PH, Canfield RE, Use of monoclonal antibodies to subunits of human chorionic gonadotropin to examine the orientation of the hormone in its complex with receptor. Proceedings of the National Academy of Sciences of the United States of America 79:2245-2249 (1982).

Moyle WR, Myers RV, Wang Y, Han Y, Lin W, Kelley GL, Ehrlich PH, Rao SN, Bernard MP, Functional homodimeric glycoprotein hormones: implications for hormone action and evolution. Chemistry & Biology 5:241-254 (1998).

Nader S, Berkowitz AS, Ochs D, Held B, Winkel CA, "Luteal-phase support in stimulated cycles in an in vitro fertilization/embryo transfer program: progesterone versus human chorionic gonadotropin," J in Vitro Fert Embryo Transf 5:81-84 (1988).

Nakabayashi K, Kudo M, Kobilka B, Hsueh AJ, "Activation of the luteinizing hormone receptor following substitution of ser-277 with selective hydrophobic residues in the ectodomain hinge region," Journal of Biological Chemistry 275:30264-30271 (2000).

Narayan P, Gray J, Puett D, "Expression of functional lutropin/choriogonadotropin receptor in the baculovirus system," Molecular & Cellular Endocrinology 117:95-100 (1996).

Narayan, Prema, et al., Functional Expression of Yoked Human Chorionic Gonadotropin in Baculovirus-Infected Insect Cells, Mol ENDO, 1995, vol. 9, No. 12, pp. 1720-1726.

Navot et al., "Ovarian Hyperstimulation syndrome in novel reproductive technologies: Prevention and treatment," Fertil Steril 58, 249-261 (1992).

Ness RB, et al., (2002), "Infertility, fertility drugs, and ovarian cancer: a pooled analysis of case control studies," Am J Epidemiol 155:217-224.

Ngan S, et al., (2007), Gestational trophoblastic neoplasia management: an update, Curr Opin Oncol 19:486-491.

O'Connell Y, McKenna TJ, Cunningham SK, "The effect of prolactin, human chorionic gonadotropin, insulin and insulin-like growth factor 1 on adrenal steroidogenesis in isolated guinea-pig adrenal cells," J Steroid Biochem Mol Biol 48:235-240 (1994).

O'Connor JF, Birken S, Lustbader JW, Krichevsky A, Chen Y, Canfield RE, "Recent advances in the chemistry and immunochemistry of human chorionic gonadotropin: impact on clinical measurements," [Review]. Endocrine Reviews 15:650-683 (1994).

Osada K, et al, (2004) "Metastatic uveal tumor secondary to testicular choriocarcinoma," Jpn J Ophthalmol 48:85-87.

Ostermeier C, et al., (1995), "Fv fragment-mediated crystallization of the membrane protein bacterial cytochrome c oxidase," Nature Structural Biology 2:842-846.

Osuga Y, Hayashi M, Kudo M, Conti M, Kobilka B, Hsueh AJ, "Co-expression of defective luteinizing hormone receptor fragments partially reconstitutes ligand-induced signal generation," Journal of Biological Chemistry 272:25006-25012 (1997).

Ozols RF (2005), "Treatment goals in ovarian cancer," Int J Gynecol Cancer 15 Suppl 1:3-11.

Padmanabhan V, et al., "An Improved in vitro Bioassay for follicle-stimulating hormone (FSH): suitable for Measurement of FSH in Unextracted Human Serum," Endocrinology. Sep. 1987;121(3):1089-98.

Parazzini F, et al., (2001), "Use of fertility drugs and risk of ovarian cancer," Hum Reprod 16:1372-1375.

Parrott JA, Doraiswamy V, Kim G, Mosher R, Skinner MK, "Expression and actions of both the follicle stimulating hormone receptor and the luteinizing hormone receptor in normal ovarian surface epithelium and ovarian cancer," Molecular & Cellular Endocrinology 172:213-222 (2001).

Pectasides D, et al., (2006), "Treatment issues in clear cell carcinoma of the ovary: a different entity?," Oncologist 11:1089-1094.

Petaja-Repo UE, Merz WE, Rajaniemi HJ, "Significance of the carbohydrate moiety of the rat ovarian luteinizing- hormone/chorionic-gonadotropin receptor for ligand-binding specificity and signal transduction," Biochemical Journal 292 ( Pt 3):839-844 (1993).

Phang T, Kundu G, Hong S, Ji I, Ji TH, "The amino-terminal region of the luteinizing hormone/choriogonadotropin receptor contacts both subunits of human choriogonadotropin. II," Photoaffinity labeling. J Biol Chem 273:13841-13847 (1998).

Pierce et al., "Glycoprotein Hormones: Structure and Function," Annu Rev Biochem 50, 465- 495 (1981).

Pollak S, Halpine S, Chait BT, Birken S, "High resolution high performance liquid chromatography fingerprinting of purified human chorionic gonadotropin demonstrates that oxidation is a cause of hormone heterogeneity," Endocrinology 126:199-208 (1990).

Powell AJ, et al., "2000 Recognition of structurally diverse substrates by type II 3-hydroxyacyl-CoA dehydrogenase (HADH II)/Amyloid-beta binding alcohol dehydrogenase (ABAD)," Journal of Molecular Biology 303:311-327.

Prast J, et al., (2008), "Human chorionic gonadotropin stimulates trophoblast invasion through extracellularly regulated kinase and AKT signaling," Endocrinology 149:979-987.

Prat J, et al., (2005), "Hereditary ovarian cancer," Hum Pathol 36:861-870.

Prinz WA, Aslund F, Holmgren A, Beckwith J, "The role of the thioredoxin and glutaredoxin pathways in reducing protein disulfide bonds in the *Escherichia coli* cytoplasm," Journal of Biological Chemistry 272:15661-15667 (1997).

Puck TT, et al., (1958), "Genetics of somatic mammalian cells. III. Long term cultivation of euploid cells from human and animal subjects," J Exp Med 108:945-956.

Puett D, Bhowmick N, Fernandez LM, Huang J, Wu C, Narayan P, "hCG-receptor binding and transmembrane signaling," Mol Cell Endocrinol 125:55-64 (1996).

Purdie D, et al., (1995), "Reproductive and other factors and risk of epithelial ovarian cancer: an Australian case control study. Survey of Women's Health Study Group," Int J Cancer 62:678-684.

Queenan et al., "Cryopreservation of all prezygotes in patients at risk of severe hyperstimulation does not eliminate the syndrome, but the chance of pregnancy are excellent with subsequent frozen-thaw transfers,"Hum Reprod 12, 1573-1576 (1997).

Rao GG, et al, (2006), "Hormonal therapy in epithelial ovarian cancer," Expert Rev Anticancer Ther 6:43-47.

Remy JJ, Bozon V, Couture L, Goxe B, Salesse R, Garnier J, "Suppression of fertility in male mice by immunization against LH receptor," J Reprod Immunol 25:63-79 (1993).

Remy JJ, Couture L, Pantel J, Haertle T, Rabesona H, Bozon V, Pajot-Augy E, Robert P, Troalen F, Salesse R, Bidart JM, "Mapping of HCG-receptor complexes," Mol Cell Endocrinol 125:79-91 (1996).

Remy JJ, Nespoulous C, Grosclaude J, Grebert D, Couture L, Pajot E, Salesse R, "Purification and Structural Analysis of a Soluble Human Chorionogonadotropin Hormone-Receptor Complex," Journal of Biological Chemistry 276:1681-1687 (2001).

Ren SG, Braunstein GD, "Progesterone and human chorionic gonadotropin do not stimulate placental proteins 12 and 14 or prolactin production by human decidual tissue in vitro," J Clin Endocrinol Metab 70:983-989 (1990).

Ribble D, et al., (2005), "A simple technique for quantifying apoptosis in 96 well plates," BMC Biotechnol 5:12.

Riman T, et al., (2004), "Review of epidemiological evidence for reproductive and hormonal factors in relation to the risk of epithelial ovarian malignancies," Acta Obstet Gynecol Scand 83:783-795.

Roche PC, Ryan RJ, McCormick DJ, "Identification of hormone-binding regions of the luteinizing hormone/human chorionic gonadotropin receptor using synthetic peptides," Endocrinology 131:268-274 (1992).

Ryu K, Gilchrist RL, Tung CS, Ji I, Ji TH, "High affinity hormone binding to the extracellular N-terminal exodomain of the follicle-stimulating hormone receptor is critically modulated by exoloop 3," J Biol Chem 273:28953-28958 (1998).

Ryu K, Lee H, Kim S, Beauchamp J, Tung CS, Isaacs NW, Ji I, Ji TH, "Modulation of high affinity hormone binding. Human choriogonadotropin binding to the exodomain of the receptor is influenced by exoloop 2 of the receptor," J Biol Chem 273:6285-6291 (1998).

Salat-Baroux et al., "Treatment of Hyperstimulation during in-vitro fertilization," Hum Reprod 5, 36-39 (1990).

Fletcher et al., "Inhibition of FSH Action on Granulosa Cells by Low molecular weight components of follicular fluid," (1982) Mol Cell Endocrinol 25, pp. 303-315.

Satake I, et al., (1994), "The aggressive treatment of choriocarcinoma of the testis associated with lung bone, and brain metastases," Int J Urol 1:87-88.

Sato N, Hotta K, Waguri S, Nitatori T, Tohyama K, Tsujimoto Y, Uchiyama Y, "Neuronal differentiation of PC12 cells as a result of prevention of cell death by bcl-2," J Neurobiol 25:1227-1234 (1994).

Schipper et al., "Application of a CHO cell line transfected with the Human FSH receptor for the measurement of specific FSH receptor activation inhibitors in human serum," (1996) J Endocrinol 150(3), pp. 505-514.

Schipper et al., "Low Levels of Follicle-Stimulating Hormone Receptor-Activation Inhibitors in Serum and Follicular Fluid from Normal Control and Anovulatory Patients with or without Polycystic Ovary Syndrome," (1997) JCEM p. 1325-1331.

Scorer CA, Buckholz RG, Clare JJ, Romanos MA, "The intracellular production and secretion of HIV-1 envelope protein in the methylotrophic yeast *Pichia pastoris*," Gene 136:111-119 (1993).

Segaloff DL, Ascoli M, "The gonadotrophin receptors: insights from the cloning of their cDNAs," [Review]. Oxford Reviews of Reproductive Biology 14:141-168 (1992).

Segaloff DL, Ascoli M, "The lutropin/choriogonadotropin receptor . . . 4 years later," [Review]. Endocr Rev 14:324-347 (1993).

Segaloff DL, Sprengel R, Nikolics K, Ascoli M, "Structure of the lutropin/choriogonadotropin receptor," [Review]. Recent Progress in Hormone Research 46:261-303 (1990).

Shi Qj, Lei ZM, Rao CV, Lin J, "Novel role of human chorionic gonadotropin in differentiation of human cytotrophoblasts," Endocrinology 132:1387-1395 (1993).

Simoni et al., "In vitro Sertoli Cell Bioassay of Follicle-Stimulating Hormone (FSH): Serum from Different animal Species Alters the Morphology of Rat Sertoli cells without Affecting their Response to FSH," (1994) Gen Comp Endocrinol, 95(1):99-108.

Smith JA, et al., (2005), "An evaluation of cytotoxicity of the taxane and platinum agents combination treatment in a panel of human ovarian carcinoma cell lines," Gynecol Oncol 98:141-145.

Song L, et al., (1996), "Structure of staphylococcal alpha-hemolysin, a heptameric transmembrane pore," Science 274:1859-1866.

Song YS, Ji I, Beauchamp J, Isaacs NW, Ji TH, "Hormone Interactions to Leu Rich Repeats in the Gonadotropin Receptors: I. Analysis of Leu Rich Repeats of Human Luteinizing Hormone/Chorionic Gonadotropin Receptor and Follicle Stimulating Hormone Receptor," Journal of Biological Chemistry, vol. 276, pp. 3426-3435 (2000).

Song YS, Ji I, Beauchamp J, Isaacs NW, Ji TH, "Hormone Interactions to Leu Rich Repeats in the Gonadotropin Receptors: II. Analysis of Leu Rich Repeat 4 of Human Luteinizing Hormone/Chorionic Gonadotropin Receptor," Journal of Biological Chemistry, vol. 276, pp. 3436-3442 (2000).

Sorkin A, Waters CM, "Endocytosis of growth factor receptors," Bioessays 15:375-382 (1993).

Stanley et al., "Selection and Charactization of Eight Phenotypically distinct lines of lectin Resistant Chinese Hamster ovary cells," Cell 6, 121-128 (1975).

Stanley, P., "Glycosylation engineering," Glycobiology 2, 99-107 (1992).

Steelman SL, et al., (1953), "Assay of follicle-stimulating hormone based of the augmentation with human chorionic gonadotropin," Endocrinology 53:604-616.

Stouffer RL, Grodin MS, Davis JR, Surwit EA, "Investigation of binding sites for follicle-stimulating hormone and chorionic gonadotropin in human ovarian cancers," J Clin Endocrinol Metab 59:441-446 (1984).

Sun E, Cohen FE,"Computer-assisted drug discovery—a review," Gene 137:127-132 (1993).

Talwar et al., "Necrosis and Inhibition of Growth of Human Lung Tumor by Anti- alpha-Human Chorionic Gonadotropin Antibody," J Natl Cancer Inst 84:42-47 (1992).

Tao YX, Bao S, Ackermann DM, Lei ZM, Rao CV, "Expression of luteinizing hormone/human chorionic gonadotropin receptor gene in benign prostatic hyperplasia and in prostate carcinoma in humans," Biology of Reproduction 56:67-72 (1997).

Tapanainen JS, et al., (1997), "Men homozygous for an inactivating mutation of the follicle-stimulating hormone (FSH) receptor gene present variable suppression of spermatogenesis and fertility," Nat Genet 15:205-207.

Tapanainen JS, Tilly JL, Vihko KK, Hsueh AJ, "Hormonal control of apoptotic cell death in the testis: gonadotropins and androgens as testicular cell survival factors," Mol Endocrinol 7:643-650 (1993).

Tegoni M, et al., (1999), "Crystal structure of a ternary complex between human chorionic gonadotropin (hCG) and two Fv fragments specific for the alpha and beta subunits," J Mol Biol 289:1375-1385.

The European Recombinant Human Chorionic Gonadotrophin Study Group, "Induction of final follicular maturation and early luteinization in women undergoing ovulation induction for assisted reproduction treatment-recombinant HCG versus urinary HCG," Hum Reprod 15:1446-1451 (2000).

The Practice Committee of the American Society for Reproductive Medicine, "Ovarian Hyperstimulation syndrome," Fertil Steril 80, 1309-1314 (2003).

Thomas D, Rozell TG, Liu X, Segaloff DL, "Mutational analyses of the extracellular domain of the full-length lutropin/choriogonadotropin receptor suggest leucine-rich repeats 1-6 are involved in hormone binding," Mol Endocrinol 10:760-768 (1996).

Tilly et al, "Expression of Recombinant Human Follicle-Stimulating Hormone Receptor: Species-Specific Ligand binding, Signal Transduction, and Identification of Multiple Ovarian Messenger Ribonucleic Acid Transcripts," Endocrinology 131(2):799-806 (1992).

Tinkle LL, et al., (2001), "Testicular choriocarcinoma metastatic to the skin: an additional case and literature review," Cutis 67:117-120.

Towbin H, et al., (1979), "Electrophoretic transfer of proteins from polyacrylamide gels to nitrocellulose sheets: procedure and some applications," Proceedings of the National Academy of Sciences of the United States of America 76:4350-4354.

Trimble RB, et al., (1991), "Structure of oligosaccharides on Saccharomyces SUC2 invertase secreted by the methylotrophic yeast *Pichia pastoris*," Journal of Biological Chemistry 266:22807-22817.

Trousdale RK, et al., (2007), "Single chain bifunctional vascular endothelial growth factor (VEGF) follicle stimulating hormone (FSH) C terminal peptide (CTP) is superior to the combination therapy of recombinant VEGF plus FSH CTP in stimulating angiogenesis during ovarian folliculogenesis," Endocrinology 148:1296-1305.

Vachon CM, et al., (2002), "Association of parity and ovarian cancer risk by family history of breast or ovarian cancer in a population based study of postmenopausal women," Epidemiology 13:66-71.

Van Damme MP, et al., A sensitive and specific in vitro bioassay method for the measurement of follicle-stimulating hormone activity, Acta Endocrinol (Jun. 1979) ;91(2):224-37.

Vannier B, et al., (1996), "Anti human FSH receptor monoclonal antibodies: immunochemical and immunocytochemical characterization of the receptor," Biochemistry 35:1358-1366.

Vardhana PA, et al., (2008), "A Unique Human Chorionic Gonadotropin Antagonist Suppresses Ovarian Hyperstimulation Syndrome (OHSS) in Rats," Endocrinology 150: 3807-3814, (2009).

Wan X, et al., (1999), "Radioimmunodetection of human trophoblastic cancer xenograft in nude mice,". Zhonghua Zhong Liu Za Zhi 21:342-344.

Wang J, et al., (2003), "Quantitative analysis of follicle stimulating hormone receptor in ovarian epithelial tumors: a novel approach to explain the field effect of ovarian cancer development in secondary mullerian systems," Int J Cancer 103:328-334.

Weenen et al., "Long Acting Follicle-Stimulating Hormone Analogs Containing N-Linked Glycosylation Exhibited Increased Bioactivity Compared with O-linked Analogs in Female Rats," Journal of Clinical Endocrinology and Metabolism:89(10):5204-5212 (2004).

Weiss HM, Haase W, Michel H, Reilander H, "Expression of functional mouse 5-HT5A serotonin receptor in the methylotrophic yeast *Pichia pastoris*: pharmacological characterization and localization," FEBS Lett 377:451-456 (1995).

Weitlauf HM, "Biology of Implatation," In: Knobil E, Neill J (eds). The Physiology of Reproduction.Raven, New York:231-262 (1988).

Willey KP (1999), "An elusive role for glycosylation in the structure and function of reproductive hormones," Hum Reprod Update 5:330-355.

Woodward BJ, Lenton EA, Turner K, "Human chorionic gonadotrophin: embryonic secretion is a time-dependent phenomenon," Human Reproduction 8:1463-1468 (1993).

Woodward BJ, Lenton EA, Turner K, Grace WF, "Embryonic human chorionic gonadotropin secretion and hatching: poor correlation with cleavage rate and morphological assessment during preimplantation development in vitro," Human Reproduction 10:1909-1914 (1994).

Wu H, Lustbader JW, Liu Y, Canfield RE, Hendrickson WA, "Structure of human chorionic gonadotropin at 2.6 A resolution from MAD analysis of the selenomethionyl protein," Structure 2:545-558 (1994).

Xin B, et al., (2007), "Anti tumor effect of non steroidal anti inflammatory drugs on human ovarian cancers," Pathol Oncol Res 13:365-369.

Yu N, et al., (2007), "Inhibition of tumor growth in vitro and in vivo by a monoclonal antibody against human chorionic gonadotropin beta," Immunol Lett 114:94-102.

Yurkova EV, Demin VV, Abdulaev NG, "Crystallization of membrane proteins: bovine rhodopsin," Biomed Sci 1:585-590 (1990).

Zeng H, Phang T, Ji I, Ji TH, "The role of the hinge region in the luteinizing hormone receptor in hormone interaction and signal generation," Journal of Biological Chemistry, vol. 276, pp. 3451-3458 (2001).

Zhang R, Buczko E, Dufau ML, "Requirement of cysteine residues in exons 1-6 of the extracellular domain of the luteinizing hormone receptor for gonadotropin binding," Journal of Biological Chemistry 271:5755-5760 (1996).

Zheng L, et al., (2004), "An efficient one step site directed and site saturation mutagenesis protocol," Nucleic Acids Res 32:e115.

Zheng W, et al., (2000), "Ovarian epithelial tumor growth promotion by follicle stimulating hormone and inhibition of the effect by luteinizing hormone," Gynecol Oncol 76:80-88.

Zirkin BR, et al., (1994), "Is FSH required for adult spermatogenesis?," J Androl 15:273-276.

Zygmunt M, et al., (1998), "Invasion of cytotrophoblastic JEG 3 cells is stimulated by hCG in vitro," Placenta 19:587-593.

Zygmunt M, et al., (2002), "Characterization of human chorionic gonadotropin as a novel angiogenic factor," J Clin Endocrinol Metab 87:5290-5296.

Cole et al., "Hyperglycosylated human chorionic gonadotropin (invasive trophoblast antigen) Immunoassay: A new basis for gestational down syndrome screening," Clinical Chemistry, vol. 45: 12, pp. 2109-2119 (1999).

Huth et al., "Bacterial expression and in vitro folding of the β-subunit of human chorionic gonadotropin (hCGβ) and functional assembly of recombinant hCGβ with hCGα," Endocrinology, vol. 135, pp. 911-918 (1994).

Li et al., "FSH stimulates ovarian cancer cell growth by action on growth factor variant receptor," Mol cell endocrinol, vol. 267, pp. 26-37 (Mar. 2007).

Osuga et al., "Derivation of functional antagonists using N-Terminal extracellular domain of gonadotropin and thyrotropin receptors," Molecular endocrinology, vol. 11: pp. 1659-1668 (1997).

Stenman et al., "Human chorionic gonadotropin in cancer," clinical biochemistry, vol. 37, pp. 549-564 (2004).

Peralta et al., "Subdermal Contraceptive implants," J. Steroid. Biochem. Molec. Biol. vol. 53, pp. 223-226 (1995).

Puthalakath et al., "Glycosylation defect in Lec1 Chinese hamster ovary mutant is due to a point mutation in N-acetylglucosaminyltransferase I Gene," The journal of Biological Chemistry, vol. 271, pp. 27818-27822 (1996).

Barnhart et al., "the Pharmacology of methotrexate," Exp. opinion Pharmacother, vol. 2(3), pp. 409-417 (2001).

Database Grencore on STN, Minegish et al., "cloning and sequencing of human Lh/hCG receptor cDNA". Biochem. Biophys. res. Commun. 1990, vol. 172, pp. 1049-1054.

Hoffmann et al., "Purification of his-tagged proteins in non-denaturing conditions suggests a convenient method for protein interaction stuide," Nucleic Acids Research, Nov. 1991, vol. 19, pp. 6337-6338.

Yding Andersen et al., "Effect of different FSH isoforms on cyclic-AMP production by mouse cumulus-oocyte-complexes: a time course study," Molecular Human reproduction vol. 7, pp. 129-135 (2001).

International Search Report mailed on May 17, 2005 for International Patent Application PCT/US2002/008985.

International Search Report mailed on Dec. 22, 2008 for International Patent Application PCT/US2008/79890.

International Search Report mailed on Oct. 29, 2009 for International Patent Application PCT/US2009/052842.

Haqq et al., "Isolation of the Rat Gene for Mullerian inhibiting substance," Genomics, vol. 12, pp. 665-669 (1992).

* cited by examiner

FIGURE 1

```
atg aag aca ctc cag ttt ttc ttc ctt ttc tgt tgc tgg aaa gca atc
                                                              48
Met Lys Thr Leu Gln Phe Phe Phe Leu Phe Cys Cys Trp Lys Ala Ile
1               5               10              15 tgc tgc aat agc tgt gag ctg acc aac atc acc att gca ata gag aaa
                                                              96
Cys Cys Asn Ser Cys Glu Leu Thr Asn Ile Thr Ile Ala Ile Glu Lys
            20              25              30 gaa gaa tgt cgt ttc tgc ata agc atc aac acc act tgg tgt gct ggc
                                                              144
Glu Glu Cys Arg Phe Cys Ile Ser Ile Asn Thr Thr Trp Cys Ala Gly
        35              40              45 tac tgc tac acc agg gat ctg gtg tat aag gac cca gcc agg ccc aaa
                                                              192
Tyr Cys Tyr Thr Arg Asp Leu Val Tyr Lys Asp Pro Ala Arg Pro Lys
    50              55              60 atc cag aaa aca tgt acc ttc aag gaa ctg gta tat gaa aca gtg aga
                                                              240
Ile Gln Lys Thr Cys Thr Phe Lys Glu Leu Val Tyr Glu Thr Val Arg
65              70              75              80 gtg ccc ggc tgt gct cac cat gca gat tcc ttg tat aca tac cca gtg
                                                              288
Val Pro Gly Cys Ala His His Ala Asp Ser Leu Tyr Thr Tyr Pro Val
            85              90              95 gcc acc cag tgt cac tgt ggc aag tgt gac agc gac agc act gat tgt
                                                              336
Ala Thr Gln Cys His Cys Gly Lys Cys Asp Ser Asp Ser Thr Asp Cys
            100             105             110 act gtg cga ggc ctg ggg ccc agc tac tgc tcc ttt ggt gaa atg aaa
                                                              384
Thr Val Arg Gly Leu Gly Pro Ser Tyr Cys Ser Phe Gly Glu Met Lys
        115             120             125 gaa gga tcc gga tcg aac gcg acg ggg tca ggt tct aat gca act tca
                                                              432
Glu Gly Ser Gly Ser Asn Ala Thr Gly Ser Gly Ser Asn Ala Thr Ser
    130             135             140 gga tcc taa
            441
Gly Ser
145
```

FIGURE 2

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
            35                  40                  45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65              70                  75                  80 gtg ccc ggc tgt gct cac cat gca gat tcc ttg tat aca tac cca gtg
288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt
336
Ala Thr Gln Cys His Cys Gly Lys Cys Asp Ser Asp Ser Thr Asp Cys
                100                 105                 110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
            115                 120                 125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
    130                 135                 140 aga tcc gga tcg aac gcg acg ggg tca ggt tct aat gca act tca gga
480
Arg Ser Gly Ser Asn Ala Thr Gly Ser Gly Ser Asn Ala Thr Ser Gly
145                 150                 155                 160 tcc taa
                486
Ser
```

FIGURE 3

| | |
|---|---|
| atg aag aca ctc cag ttt ttc ttc ctt ttc tgt tgc tgg aaa gca atc<br>Met Lys Thr Leu Gln Phe Phe Phe Leu Phe Cys Cys Trp Lys Ala Ile<br>1                        5                                  10                              15 | 48 |
| tgc tgc aat agc tgt gag ctg acc aac atc acc att gca ata gag aaa<br>Cys Cys Asn Ser Cys Glu Leu Thr Asn Ile Thr Ile Ala Ile Glu Lys<br>               20                         25                          30 | 96 |
| gaa gaa tgt cgt ttc tgc ata agc atc aac acc act tgg tgt gct ggc<br>Glu Glu Cys Arg Phe Cys Ile Ser Ile Asn Thr Thr Trp Cys Ala Gly<br>         35                        40                            45 | 144 |
| tac tgc tac acc agg gat ctg gtg tat aag gac cca gcc agg ccc aaa<br>Tyr Cys Tyr Thr Arg Asp Leu Val Tyr Lys Asp Pro Ala Arg Pro Lys<br>     50                      55                        60 | 192 |
| atc cag aaa aca tgt acc ttc aag gaa ctg gta tat gaa aca gtg aga<br>Ile Gln Lys Thr Cys Thr Phe Lys Glu Leu Val Tyr Glu Thr Val Arg<br>65                       70                        75                  80 | 240 |
| gtg ccc ggc tgt gct cac cat gca gat tcc ttg tat aca tac cca gtg<br>Val Pro Gly Cys Ala His His Ala Asp Ser Leu Tyr Thr Tyr Pro Val<br>               85                         90                        95 | 288 |
| gcc acc cag tgt cac tgt ggc aag tgt gac agc gac agc act gat tgt<br>Ala Thr Gln Cys His Cys Gly Lys Cys Asp Ser Asp Ser Thr Asp Cys<br>             100                     105                    110 | 336 |
| act gtg cga ggc ctg ggg ccc agc tac tgc tcc ttt ggt gaa atg aaa<br>Thr Val Arg Gly Leu Gly Pro Ser Tyr Cys Ser Phe Gly Glu Met Lys<br>         115                     120                    125 | 384 |
| gaa gga tcc ccc cgc ttc cag gac tcc tct tca aag gcc cct ccc<br>Glu Gly Ser Pro Arg Phe Gln Asp Ser Ser Ser Lys Ala Pro Pro<br>     130                     135                    140 | 432 |
| ccc agc ctt cca agc cca tcc cga ctc ccg ggg ccc tcg gac acc ccg<br>Pro Ser Leu Pro Ser Pro Ser Arg Leu Pro Gly Pro Ser Asp Thr Pro<br>145                       150                     155                  160 | 480 |
| atc ctc cca caa act agt gct cct gat gtg cag gat tgc cca gaa tgc<br>Ile Leu Pro Gln Thr Ser Ala Pro Asp Val Gln Asp Cys Pro Glu Cys<br>             165                     170                    175 | 528 |
| acg cta cag gaa aac cca ttc ttc tcc cag ccg ggt gcc cca ata ctt<br>Thr Leu Gln Glu Asn Pro Phe Phe Ser Gln Pro Gly Ala Pro Ile Leu<br>         180                     185                    190 | 576 |
| cag tgc atg ggc tgc tgc ttc tct aga gca tat ccc act cca cta agg<br>Gln Cys Met Gly Cys Cys Phe Ser Arg Ala Tyr Pro Thr Pro Leu Arg<br>             195                     200                    205 | 624 |
| tcc aag aag acg atg ttg gtc caa aag aac gtc acc tca gag tcc act<br>Ser Lys Lys Thr Met Leu Val Gln Lys Asn Val Thr Ser Glu Ser Thr<br>     210                     215                    220 | 672 |
| tgc tgt gta gct aaa tca tat aac agg gtc aca gta atg ggg ggt ttc<br>Cys Cys Val Ala Lys Ser Tyr Asn Arg Val Thr Val Met Gly Gly Phe<br>225                       230                     235                  240 | 720 |
| aaa gtg gag aac cac acg gcg tgc cac tgc agt act tgt tat tat cac<br>Lys Val Glu Asn His Thr Ala Cys His Cys Ser Thr Cys Tyr Tyr His<br>             245                     250                    255 | 768 |
| aaa tct taa<br>Lys Ser | 777 |

FIGURE 4

```
atg aag aca ctc cag ttt ttc ttc ctt ttc tgt tgc tgg aaa gca atc
48
Met Lys Thr Leu Gln Phe Phe Phe Leu Phe Cys Cys Trp Lys Ala Ile
1                5                  10                 15 tgc tgc aat agc tgt gag ctg acc aac atc acc att gca ata gag aaa
96
Cys Cys Asn Ser Cys Glu Leu Thr Asn Ile Thr Ile Ala Ile Glu Lys
            20                 25                 30 gaa gaa tgt cgt ttc tgc ata agc atc aac acc act tgg tgt gct ggc
144
Glu Glu Cys Arg Phe Cys Ile Ser Ile Asn Thr Thr Trp Cys Ala Gly
        35                 40                 45 tac tgc tac acc agg gat ctg gtg tat aag gac cca gcc agg ccc aaa
192
Tyr Cys Tyr Thr Arg Asp Leu Val Tyr Lys Asp Pro Ala Arg Pro Lys
    50                 55                 60 atc cag aaa aca tgt acc ttc aag gaa ctg gta tat gaa aca gtg aga
240
Ile Gln Lys Thr Cys Thr Phe Lys Glu Leu Val Tyr Glu Thr Val Arg
65             70                 75                 80 gtg ccc ggc tgt gct cac cat gca gat tcc ttg tat aca tac cca gtg
288
Val Pro Gly Cys Ala His His Ala Asp Ser Leu Tyr Thr Tyr Pro Val
                85                 90                 95 gcc acc cag tgt cac tgt ggc aag tgt gac agc gac agc act gat tgt
336
Ala Thr Gln Cys His Cys Gly Lys Cys Asp Ser Asp Ser Thr Asp Cys
            100                105                110 act gtg cga ggc ctg ggg ccc agc tac tgc tcc ttt ggt gaa atg aaa
384
Thr Val Arg Gly Leu Gly Pro Ser Tyr Cys Ser Phe Gly Glu Met Lys
        115                120                125 gaa gga tcc gga tcg aac gcg acg ggg tca ggt tct aat gca act tca
432
Glu Gly Ser Gly Ser Asn Ala Thr Gly Ser Gly Ser Asn Ala Thr Ser
    130                135                140 gga tcc act agt gct cct gat gtg cag gat tgc cca gaa tgc acg cta
480
Gly Ser Thr Ser Ala Pro Asp Val Gln Asp Cys Pro Glu Cys Thr Leu
145                150                155                160 cag gaa aac cca ttc ttc tcc cag ccg ggt gcc cca ata ctt cag tgc
528
Gln Glu Asn Pro Phe Phe Ser Gln Pro Gly Ala Pro Ile Leu Gln Cys
                165                170                175 atg ggc tgc tgc ttc tct aga gca tat ccc act cca cta agg tcc aag
576
Met Gly Cys Cys Phe Ser Arg Ala Tyr Pro Thr Pro Leu Arg Ser Lys
            180                185                190 aag acg atg ttg gtc caa aag aac gtc acc tca gag tcc act tgc tgt
624
Lys Thr Met Leu Val Gln Lys Asn Val Thr Ser Glu Ser Thr Cys Cys
        195                200                205 gta gct aaa tca tat aac agg gtc aca gta atg ggg ggt ttc aaa gtg
672
Val Ala Lys Ser Tyr Asn Arg Val Thr Val Met Gly Gly Phe Lys Val
    210                215                220 gag aac cac acg gcg tgc cac tgc agt act tgt tat tat cac aaa tct
720
Glu Asn His Thr Ala Cys His Cys Ser Thr Cys Tyr Tyr His Lys Ser
225                230                235                240 taa
723
```

FIGURE 5

```
atg aag aca ctc cag ttt ttc ttc ctt ttc tgt tgc tgg aaa gca atc         48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa         96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc        144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa        192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga        240
Ile Gln Lys Thr Cys Thr Phe Lys Glu Leu Val Tyr Glu Thr Val Arg
65              70                  75                  80 gtg ccc ggc tgt gct cac cat gca gat tcc ttg tat aca tac cca gtg        288
Val Pro Gly Cys Ala His His Ala Asp Ser Leu Tyr Thr Tyr Pro Val
            85                  90                  95 gcc acc cag tgt cac tgt ggc aag tgt gac agc gac agc act gat tgt        336
Ala Thr Gln Cys His Cys Gly Lys Cys Asp Ser Asp Ser Thr Asp Cys
        100                 105                 110 act gtg cga ggc ctg ggg ccc agc tac tgc tcc ttt ggt gaa atg aaa        384
Thr Val Arg Gly Leu Gly Pro Ser Tyr Cys Ser Phe Gly Glu Met Lys
    115                 120                 125 gaa gga tcc gga tcg aac gcg acg ggg tca ggt tct aat gca act tca        432
Glu Gly Ser Gly Ser Asn Ala Thr Gly Ser Gly Ser Asn Ala Thr Ser
130                 135                 140 aga tcc gga tcg aac gcg acg ggg tca ggt tct aat gca act tca gga        480
Arg Ser Gly Ser Asn Ala Thr Gly Ser Gly Ser Asn Ala Thr Ser Gly
145                 150                 155                 160 tcc act agt gct cct gat gtg cag gat tgc cca gaa tgc acg cta cag        528
Ser Thr Ser Ala Pro Asp Val Gln Asp Cys Pro Glu Cys Thr Leu Gln
            165                 170                 175 gaa aac cca ttc ttc tcc cag ccg ggt gcc cca ata ctt cag tgc atg        576
Glu Asn Pro Phe Phe Ser Gln Pro Gly Ala Pro Ile Leu Gln Cys Met
        180                 185                 190 ggc tgc tgc ttc tct aga gca tat ccc act cca cta agg tcc aag aag        624
Gly Cys Cys Phe Ser Arg Ala Tyr Pro Thr Pro Leu Arg Ser Lys Lys
    195                 200                 205 acg atg ttg gtc caa aag aac gtc acc tca gag tcc act tgc tgt gta        672
Thr Met Leu Val Gln Lys Asn Val Thr Ser Glu Ser Thr Cys Cys Val
210                 215                 220 gct aaa tca tat aac agg gtc aca gta atg ggg ggt ttc aaa gtg gag        720
Ala Lys Ser Tyr Asn Arg Val Thr Val Met Gly Gly Phe Lys Val Glu
225                 230                 235                 240 aac cac acg gcg tgc cac tgc agt act tgt tat tat cac aaa tct taa       768
Asn His Thr Ala Cys His Cys Ser Thr Cys Tyr Tyr His Lys Ser
            245                 250                 255
```

FIGURE 6
A) 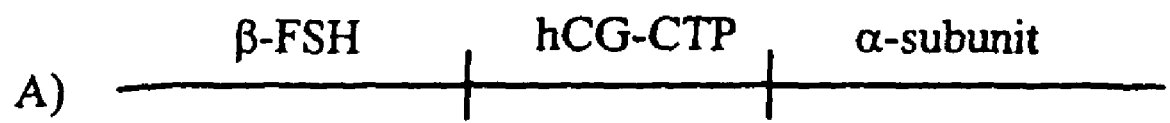
B) 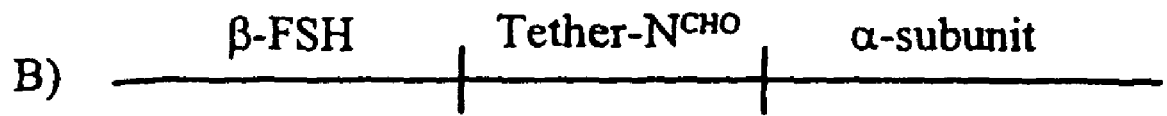

FIGURE 12

Table I: Pharmacokinetic parameter estimates after IV bolus injection of r-hFSH-CTP and r-hFSH at a dose of 10 IU/kg

| PARAMETER | r-hFSH-CTP | r-hFSH |
|---|---|---|
| $T_{1/2\ alpha\ (distribution)}$ (hr) | 3.16 | 1.39 |
| $T_{1/2\ beta\ (elimination)}$ (hr) | 35.29 | 8.25 |
| AUC (mIU/ml·d) | 278[a] | 38.8 |
| Clearance (l/kg·hr) | 1.50[b] | 10.74 |

[a] see discussion
[b] see discussion

FIGURE 13

Table II: Mean pharmacokinetic parameter estimates after subcutaneous injection of r-hFSH-CTP and r-hFSH at a dose of 10 IU/kg.

| PARAMETER | r-hFSH-CTP (n=4) | r-hFSH (n=2) |
|---|---|---|
| $T_{1/2\ elimination}$ (hrs) | 35.23 | 15.74 |
| $T_{1/2\ absorption}$ (hrs) | 5.04 | 1.75 |
| $C_{max}$ (mIU/ml) | 101.26[a] | 25.77 |
| $T_{max}$ (hours) | 16.39 | 5.95 |
| AUC (mIU/ml·d) | 275.31[a] | 30.96 |
| Bioavailability (%) (AUCsc/AUCiv) | 99 | 80 |

[a] see discussion

FIGURE 14

Beta hCG

```
1                              10         CHO
Ser-Lys-Glu-Pro-Leu-Arg-Pro-Arg-Cys-Arg-Pro-Ile-Asn-Ala-Thr-Leu-Ala-
          20                              CHO
Val-Glu-Lys-Glu-Gly-Cys-Pro-Val-Cys-Ile-Thr-Val-Asn-Thr-Thr-Ile-Cys-
                    40                                        50
Ala-Gly-Tyr-Cys-Pro-Thr-Met-Thr-Arg-Val-Leu-Gln-Gly-Val-Leu-Pro-Ala-
                              60
Leu-Pro-Gln-Val-Val-Cys-Asn-Tyr-Arg-Asp-Val-Arg-Phe-Glu-Ser-Ile-Arg-
        70                                    80
Leu-Pro-Gly-Cys-Pro-Arg-Gly-Val-Asn-Pro-Val-Val-Ser-Tyr-Ala-Val-Ala-
                    90                                      100
Leu-Ser-Cys-Gln-Cys-Ala-Leu-Cys-Arg-Arg-Ser-Thr-Thr-Asp-Cys-Gly-Gly-
                                      110
Pro-Lys-Asp-His-Pro-Leu-Thr-Cys-Asp-Asp-Pro-Arg-Phe-Gln-Asp-Ser-Ser-
120  CHO                        CHO          130    CHO
Ser-Ser-Lys-Ala-Pro-Pro-Pro-Ser-Leu-Pro-Ser-Pro-Ser-Arg-Leu-Pro-Gly-
  CHO      140              145
Pro-Ser-Asp-Thr-Pro-Ile-Leu-Pro-Gln
```

FIGURE 15
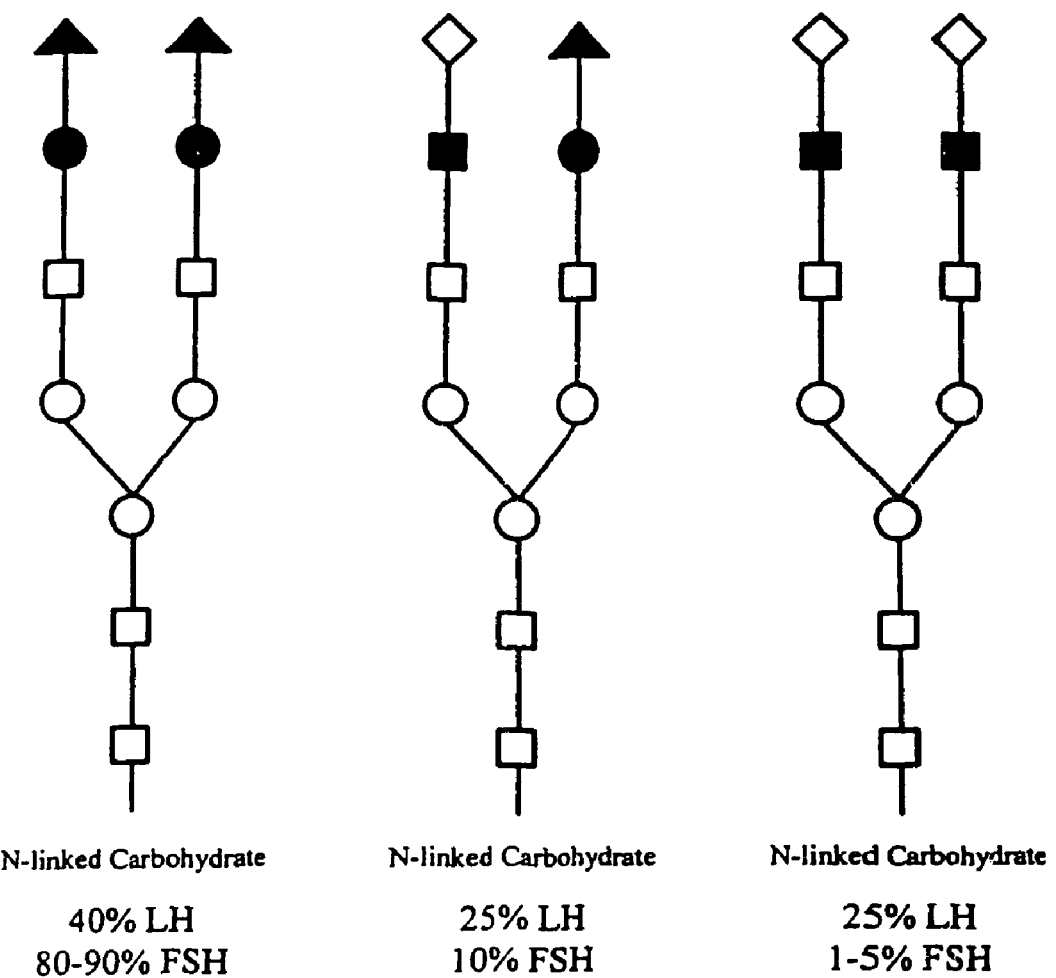
N-linked Carbohydrate
40% LH
80-90% FSH
N-linked Carbohydrate
25% LH
10% FSH
N-linked Carbohydrate
25% LH
1-5% FSH
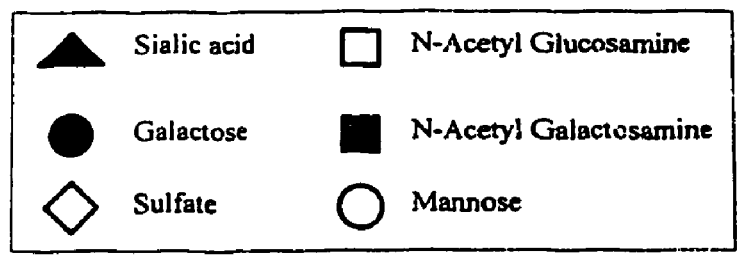

FIGURE 16
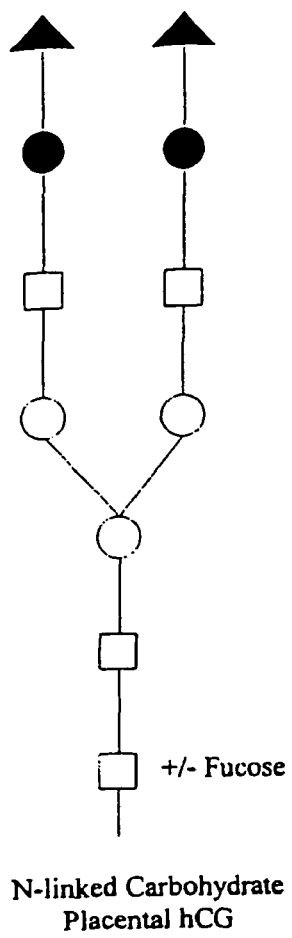
N-linked Carbohydrate
Placental hCG
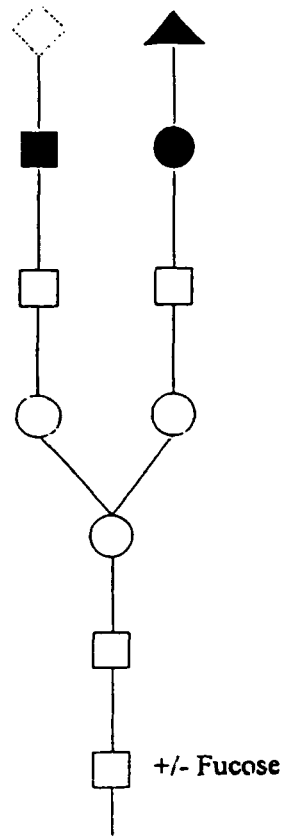
N-linked Carbohydrate
Pituitary hCG
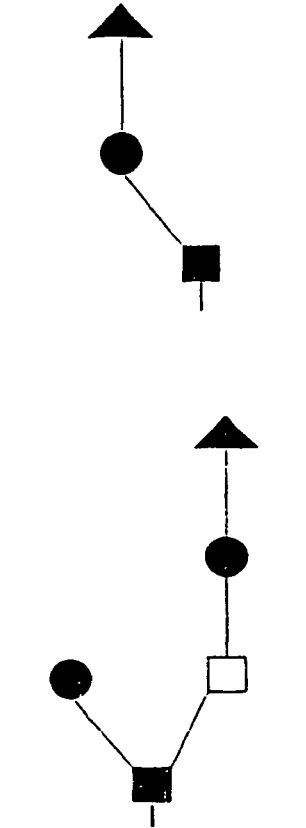
O-linked Carbohydrate
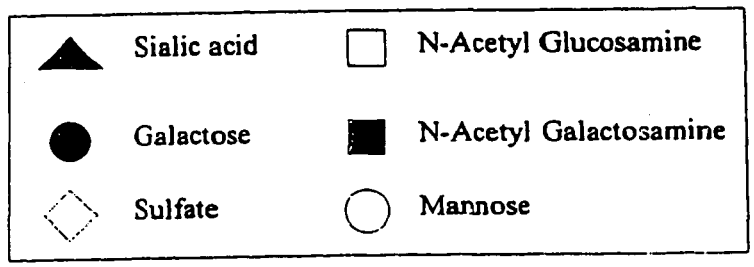

FIGURE 17

```
     M   K   T   L   Q   F   F   F   L   F   C   C   W
 1   atg aag aca ctc cag ttt ttc ttc ctt ttc tgt tgc tgg   39

K   A   I   C   C   N   S   C   E   L   T   N   I
40   aaa gca atc tgc tgc aat agc tgt gag ctg acc aac atc   78

T   I   A   I   E   K   E   E   C   R   F   C   I
79   acc att gca ata gag aaa gaa gaa tgt cgt ttc tgc ata  117

S   I   N   T   T   W   C   A   G   Y   C   Y   T
118  agc atc aac acc act tgg tgt gct ggc tac tgc tac acc  156

R   D   L   V   Y   K   D   P   A   R   P   K   I
157  agg gat ctg gtg tat aag gac cca gcc agg ccc aaa atc  195

Q   K   T   C   T   F   K   E   L   V   Y   E   T
196  cag aaa aca tgt acc ttc aag gaa ctg gta tat gaa aca  234

V   R   V   P   G   C   A   H   H   A   D   S   L
235  gtg aga gtg ccc ggc tgt gct cac cat gca gat tcc ttg  273

Y   T   Y   P   V   A   T   Q   C   H   C   G   K
274  tat aca tac cca gtg gcc acc cag tgt cac tgt ggc aag  312

C   D   S   D   S   T   D   C   T   V   R   G   L
313  tgt gac agc gac agc act gat tgt act gtg cga ggc ctg  351

G   P   S   Y   C   S   F   G   E   M   K   E   *
352  ggg ccc agc tac tgc tcc ttt ggt gaa atg aaa gaa taa  390

```
      M   D   Y   Y   R   K   Y   A   A   I   F   L   V
  1  atg gat tac tac aga aaa tat gca gct atc ttt ctg gtc   39

T   L   S   V   F   L   H   V   L   H   S   A   P
 40  aca ttg tcg gtg ttt ctg cat gtt ctc cat tcc gct cct   78

D   V   Q   D   C   P   E   C   T   L   Q   E   N
 79  gat gtg cag gat tgc cca gaa tgc acg cta cag gaa aac  117

P   F   F   S   Q   P   G   A   P   I   L   Q   C
118  cca ttc ttc tcc cag ccg ggt gcc cca ata ctt cag tgc  156

M   G   C   C   F   S   R   A   Y   P   T   P   L
157  atg ggc tgc tgc ttc tct aga gca tat ccc act cca cta  195

R   S   K   K   T   M   L   V   Q   K   N   V   T
196  agg tcc aag aag acg atg ttg gtc caa aag aac gtc acc  234

S   E   S   T   C   C   V   A   K   S   Y   N   R
235  tca gag tcc act tgc tgt gta gct aaa tca tat aac agg  273

V   T   V   M   G   G   F   K   V   E   N   H   T
274  gtc aca gta atg ggg ggt ttc aaa gtg gag aac cac acg  312

A   C   H   C   S   T   C   Y   Y   H   K   S   *
313  gcg tgc cac tgc agt act tgt tat tat cac aaa tct taa  351

| Table 3: Mean PK parameters (n=3) of serum hFSH after IV injections of hFSH, FSH-CTP and N2 in the dose of 2800 ng/rat to immature female rats (21 days old). | | | |
|---|---|---|---|
| *Parameters | hFSH | FSH-CTP | N-2 |
| $AUC_{0\text{-infinity}}$ (ng/h/ml) | 1491 | 3887 | 4802 |
| t1/2(Beta phase)(h) | 3.7 | 7.1 | 7.3 |

LONG-ACTING FOLLICLE STIMULATING HORMONE ANALOGUES AND USES THEREOF

This application is a continuation of U.S. Ser. No. 10/112,321, filed Mar. 27, 2002, now U.S. Pat. No. 7,081,446 B2, issued Jul. 25, 2006, which is a continuation-in-part of U.S. Ser. No. 10/062,910, filed Jan. 31, 2002, now abandoned, the contents of each of which are hereby incorporated in their entirety into this application by reference.

The invention described herein was made with government support under grant number DK-51266 from the National Institutes of Health. Accordingly, the United States government has certain rights in this invention.

Throughout this application, various publications are referenced by author and publication date. Full citations for these publications may be found at the end of the specification immediately preceding the claims. The disclosure of these publications is hereby incorporated by reference into this application to describe more fully the art to which this invention pertains.

SEQUENCE LISTING

The instant application contains a Sequence Listing which has been submitted via EFS-Web and is hereby incorporated by reference in its entirety. Said ASCII copy, created on Mar. 2, 2010, is named 19240856.txt, and is 33,784 bytes in size.

BACKGROUND OF THE INVENTION

The pituitary glycoprotein hormone, follicle stimulating hormone (FSH), is a heterodimer comprised of two non-covalently bound subunits, α and β (Pierce et al, 1981). The α-subunit is interchangeable among the hormones of this family, which include luteinizing hormone (LH), thyrotropin stimulating hormone (TSH) and chorionic gonadotropin (CG), in addition to FSH. The β-subunit, on the other hand, is unique to each hormone and is primarily responsible for the biological specificity of hormone action (see FIGS. 17 and 18 for the sequences of the hFSH α and β subunits, respectively).

Human FSH (hFSH) contains four N-linked carbohydrate moieties, two on each of the α- and β-subunits. A schematic of the carbohydrate moieties on hLH and hFSH is shown in FIG. 15. While the functional significance of these moieties is poorly understood, they are likely to be important for proper protein folding, subunit assembly and secretion of the hormone (Suganuma et al 1989; Feng et al, 1995). The carbohydrate moieties may also be obligatory for signal transduction, although partially deglycosylated hormones show preserved receptor binding (Calvo et al, 1986; Sairam et al, 1982).

Among the glycoprotein hormones, hCG is known to have the longest circulating half-life. This has been attributed to the presence of four O-linked glycosylation sites on the carboxy-terminal peptide (CTP) sequence of the β-subunit, corresponding to amino acids 113-145 (Matzuk et al, 1990). In contrast with N-linked sugars, deglycosylation of O-linked moieties does not affect signal transduction, and hCG devoid of this extension maintains its in vitro bioactivity. Schematic examples of N-linked and O-linked carbohydrates are shown in FIG. 16.

Instead, the importance of the O-linked sugars lies in providing enhanced stability of the hormone in vivo. This was initially deduced from comparisons between hCG and hLH, whose biological activity and β subunits are remarkably similar but whose serum half lives are dramatically different. The β subunits of hCG and hLH share greater than 85% sequence identity through the N-terminal 113 amino acids (Pierce et al, 1981). In addition, these two hormones share a common receptor and elicit similar biologic activity following receptor binding. However, the serum half-life of hCG is almost five-times that of hLH (Porchet et al, 1995; Saal et al, 1991; Yen et al, 1968). The primary structural difference between β-CG and β-hLH is the additional carboxy-terminal amino acids comprising the CTP sequence of β-hCG. This carboxy-terminal peptide, specifically its O-linked glycosylation sequences, is thus likely to be responsible for both the decreased metabolism and excretion of hCG, and thus also for its notably increased serum half-life over the relatively transient hLH.

The importance of the CTP in promoting hormone stability was demonstrated by the construction of a fusion protein consisting of the CTP portion of the β-subunit of hCG and the carboxy terminus of β-hFSH. This β-hFSH-CTP fusion produced a long-acting hFSH agonist which was able to dimerize with a coexpressed α-subunit to produce a functional FSH hormone (Fares et al, 1992). Importantly, this β-hFSH-CTP demonstrated similar in vitro bioactivity and substantially increased in vivo bioactivity compared with preparations of native hFSH.

Thus, merely adding the CTP sequence to β-hFSH was sufficient to increase the biological activity of the hormone, most likely through an increase in serum-half life. Indeed, recent pharmacokinetic parameter estimates in humans have demonstrated that this β-hFSH-CTP analog has an elimination half-life of 2 to 3 times longer than that of native recombinant hFSH (Bouloux et al, 2001).

Current pharmacologic formulations of FSH include purified urinary derivatives and, more recently, recombinant human FSH (r-hFSH). Due to its relatively short half-life, hFSH must be administered as a daily intramuscular or subcutaneous injection, often for 8 to 12 days when used for ovulation induction (LeContonnec et al, 1994). These regimens of controlled ovarian hyperstimulation are associated with a number of side effects, including local irritation and discomfort, which result in poor compliance and a reduction in therapeutic efficacy.

A long-acting FSH formulation requiring less frequent administration would provide an important development for subjects requiring gonadotropin replacement therapy.

The present invention is based on the surprising and unexpected finding that the addition of multiple N-linked glycosylation sequences confers increased protein stability, as demonstrated by an increased in vivo serum half-life. Importantly, the addition of these novel N-linked moieties does not alter the biological activity of the hFSH analogues disclosed herein, as might have been expected given the known importance of N-linked sugars in signal transduction initiated by gonadotropin hormones. Thus, the present invention provides novel hFSH analogues that have an increased serum half-life without sacrificing biological activity, offering a significant advantage over current technologies in gonadotropin replacement therapy. Such therapies are important for the treatment of infertility and have particular relevance to increasing the efficacy of in vitro fertilization protocols, both in agriculturally important mammals and in humans.

SUMMARY OF THE INVENTION

This invention provides a synthetic FSH comprising a β-FSH subunit, an α-FSH subunit and a half-life-increasing moiety, wherein the β-FSH subunit, α-FSH subunit and half-life-increasing moiety are covalently bound.

This invention also provides a synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser (SEQ ID NO:9).

This invention also provides a synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ ID NO:9), wherein the β-FSH subunit, α-FSH subunit and polypeptide segment are covalently bound.

This invention also provides a pharmaceutical composition comprising a synthetic FSH of the instant invention and a pharmaceutically acceptable carrier.

This invention further provides an article of manufacture comprising (a) the instant pharmaceutical composition, and (b) a label and/or instructions indicating a use of the pharmaceutical composition for the enhancement of fertility, egg production and/or spermatogenesis.

This invention provides nucleic acids encoding the instant synthetic FSH polypeptides, as well as expression vectors and suitable host cells for expressing these polypeptides.

This invention also provides a method for producing the polypeptides of the instant invention that comprises growing a suitable host cell transfected with a vector encoding the polypeptide under conditions permitting its expression and recovering the polypeptide so expressed.

This invention additionally provides a method for producing a synthetic FSH, which comprises co-expressing (i) a nucleic acid which encodes an α-FSH subunit, and (ii) a nucleic acid which encodes a polypeptide comprising a β-FSH subunit and a polypeptide segment comprising the amino acid sequence ser-gly-ser-asn-ala-thr-gly-ser-gly-ser-asn-ala-thr-ser-gly-ser (SEQ ID NO:9), under conditions permitting such co-expression; and recovering the synthetic FSH so produced.

This invention provides a method for increasing a subject's fertility which comprises administering to the subject an amount of the instant synthetic FSH effective to enhance the subject's fertility.

This invention also provides a method for increasing a subject's spermatogenesis which comprises administering to the subject an amount of the instant synthetic FSH effective to enhance the subject's spermatogenesis.

This invention also provides a method for increasing a subject's egg production which comprises administering to the subject an amount of the instant synthetic FSH effective to enhance the subject's egg production.

Finally, this invention provides a method of increasing the half-life of a molecule in a subject, which method comprises glycosylating the molecule in a manner effective to increase the molecule's half-life.

BRIEF DESCRIPTION OF THE FIGURES

FIG. 1: Nucleotide (SEQ ID NO: 1) and predicted amino acid sequence (SEQ ID NO: 10) of the fusion protein β-hFSH-N2. The N2 sequence is amino acids 130 through 146.

FIG. 2: Nucleotide (SEQ ID NO: 2) and predicted amino acid sequence (SEQ ID NO: 11) of the fusion protein β-hFSH N4. The N4 sequence is amino acids 130 through 161.

FIG. 3: Nucleotide (SEQ ID NO: 3) and predicted amino acid sequence (SEQ ID NO: 12) of the fusion protein β-hFSH-CTP-α-hFSH.

FIG. 4: Nucleotide (SEQ ID NO: 4) and predicted amino acid sequence (SEQ ID NO: 13) of the fusion protein β-hFSH-N2-α-hFSH.

FIG. 5: Nucleotide (SEQ ID NO: 5) and predicted amino acid sequence (SEQ ID NO: 14) of the fusion protein β-hFSH-N4-α-hFSH.

FIG. 6: (Panel A) Schematic β-hFSH-CTP-α construct; (Panel B) Schematic β-hFSH-N2/N4-α construct.

FIG. 12: Pharmacokinetic parameter estimates after IV bolus injection of the FSH analogue, β-hFSH-CTP-α-hFSH (r-hFSH-CTP), or the control recombinant hFSH protein (r-hFSH), each at a dose of 10 IU/kg.

FIG. 13: Mean pharmacokinetic parameter estimates after subcutaneous injection of the FSH analogue, β-hFSH-CTP-α-hFSH (r-hFSH-CTP), or the control recombinant hFSH protein (r-hFSH), each at a dose of 10 IU/kg.

FIG. 14: Amino acid sequence of β-hCG (SEQ ID NO:6), wherein CHO is a glycosylation site and the black shading corresponds to the CTP. N-linked glycosylation is present on Asn, and O-linked glycosylation is present on Ser.

FIG. 15: Schematic of the carbohydrate moieties on both hLH and hFSH and some of the microheterogeneity which results in the wide range of isoelectric points in the glycoprotein hormones.

FIG. 16: Schematic examples of N-linked and O-linked carbohydrates.

FIG. 17: Nucleotide (SEQ ID NO: 7) and amino acid sequence (SEQ ID NO: 15) of β-hFSH. The signal sequence corresponds to the sequence beginning with the methionine at position 1 and ending with the cysteine at position 18.

FIG. 18: Nucleotide (SEQ ID NO: 8) and amino acid sequence (SEQ ID NO: 16) of α-hFSH. The signal sequence corresponds to the sequence beginning with the methionine at position 1 and ending with the serine at position 24.

FIG. 21: Mean pharmacokinetic parameters of serum hFSH following a single IV injection of either the control, recombinant human FSH (hFSH), FSH-CTP or N-2. Twenty-one day old female rats were injected at a dose of 2800 ng/rat.

DETAILED DESCRIPTION OF THE INVENTION

Figure 7:
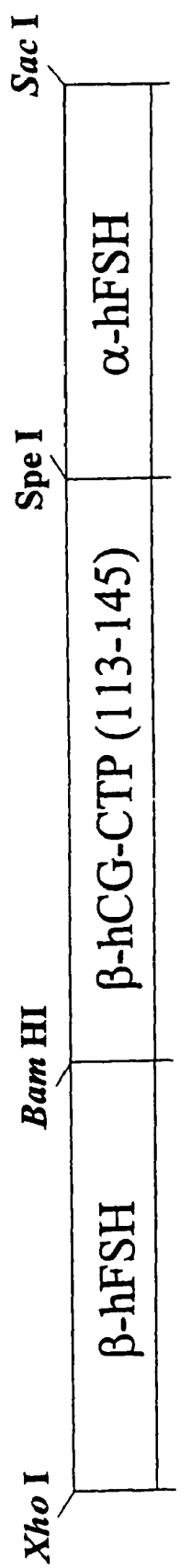
FIG. 7: Schematic of β-hFSH-CTP-α-hFSH construct with locations of restriction sites.

This invention provides FSH analogues, also referred to herein as "synthetic FSH." These analogues represent a significant advance over known agents for several reasons.

Among these is the fact that these analogues can be expressed as single chain polypeptides having both the α and β subunits of FSH and a polypeptide segment having either O- or N-linked glycosylation sites. These single chain analogues are fully functional hormones that are more easily purified than analogues requiring separate expression and subsequent dimerization of the α and β subunits.

Also, the use of N-linked glycosylation sites in the polypeptide segment offers a number of advantages over the use of an hCG carboxy-terminal peptide sequence alone. Specifically, N-linked glycosylation sites are discreet and well-defined. This permits the facile construction of half-life-increasing moieties having one or more glycosylation sites at predetermined locations along a polypeptide, for example. Glycosylation using N-linked sites permits fine-tuning the half-life and thus the bioactivity of the instant synthetic hormones to meet particular therapeutic needs.

DEFINITIONS

The terms "amino acid," "amino acid residue" or "residue" are used interchangeably herein to refer to an amino acid that is incorporated into a protein, polypeptide or peptide. The amino acid can be, for example, a naturally occurring amino acid or an analog of a natural amino acid acid that can function in a similar manner as the naturally occurring amino acid.

As used herein, "CTP" means the carboxy-terminal peptide of β-hCG, corresponding to amino acid residues 113-145. This portion of hCG contains multiple O-linked glycosylation sites (see FIG. 14).

The letter "h" is used herein to designate the human isoform of a protein or polypeptide. For example, hFSH means human follicle stimulating hormone. FSH is a pituitary glycoprotein essential for follicular growth as well as spermatogenesis, comprised of a noncovalently linked heterodimer of two peptide subunits, α and β. The β subunit is specific to FSH and thus determines its biological activity, while the α subunit is common to the other members of this glycoprotein family, for example, luteinizing hormone (LH), chorionic gonadotrophin (CG) and thyroid-stimulating hormone (TSH).

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

As used herein, "serum half-life", abbreviated "$t_{1/2}$", means elimination half-life, i.e., the time at which the serum concentration of an agent has reached one-half its initial or maximum value. The term "increased serum half-life" used herein in reference to a synthetic agent means that the synthetic agent is cleared at a slower rate than either the non-synthetic, endogenous agent or the recombinantly produced version thereof. For example, the $t_{1/2}$ of a synthetic FSH, e.g., hFSH-N2, in a subject would be "increased" if it exceeds the $t_{1/2}$ of either endogenous FSH or recombinantly produced native FSH.

As used herein, "suitable host cells" include, but are not limited to, bacterial cells, yeast cells, fungal cells, insect cells, and mammalian cells. Mammalian cells can be transfected by methods well-known in the art such as calcium phosphate precipitation, electroporation and microinjection.

As used herein, "vector" means any nucleic acid vector known in the art. Such vectors include, but are not limited to, plasmid vectors, cosmid vectors, and bacteriophage vectors.

Units, prefixes and symbols may be denoted in their SI accepted form. Unless otherwise indicated, nucleic acid sequences are written left to right in 5' to 3' orientation and amino acid sequences are written left to right in amino- to carboxy-terminal orientation. Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

In this invention, administering the instant pharmaceutical composition can be effected or performed using any of the various methods and delivery systems known to those skilled in the art. The administering can be performed, for example, intravenously, orally, via implant, transmucosally, transdermally, intramuscularly, and subcutaneously. In addition, the instant pharmaceutical compositions ideally contain one or more routinely used pharmaceutically acceptable carriers. Such carriers are well known to those skilled in the art. The following delivery systems, which employ a number of routinely used carriers, are only representative of the many embodiments envisioned for administering the instant composition.

Injectable drug delivery systems include solutions, suspensions, gels, microspheres and polymeric injectables, and can comprise excipients such as solubility-altering agents (e.g., ethanol, propylene glycol and sucrose) and polymers (e.g., polycaprylactones and PLGA's). Implantable systems include rods and discs, and can contain excipients such as PLGA and polycaprylactone.

Oral delivery systems include tablets and capsules. These can contain excipients such as binders (e.g., hydroxypropylmethylcellulose, polyvinyl pyrilodone, other cellulosic materials and starch), diluents (e.g., lactose and other sugars, starch, dicalcium phosphate and cellulosic materials), disintegrating agents (e.g., starch polymers and cellulosic materials) and lubricating agents (e.g., stearates and talc).

Transmucosal delivery systems include patches, tablets, suppositories, pessaries, gels and creams, and can contain excipients such as solubilizers and enhancers (e.g., propylene glycol, bile salts and amino acids), and other vehicles (e.g., polyethylene glycol, fatty acid esters and derivatives, and hydrophilic polymers such as hydroxypropylmethylcellulose and hyaluronic acid).

Dermal delivery systems include, for example, aqueous and nonaqueous gels, creams, multiple emulsions, microemulsions, liposomes, ointments, aqueous and nonaqueous solutions, lotions, aerosols, hydrocarbon bases and powders, and can contain excipients such as solubilizers, permeation enhancers (e.g., fatty acids, fatty acid esters, fatty alcohols and amino acids), and hydrophilic polymers (e.g., polycarbophil and polyvinylpyrolidone).

Solutions, suspensions and powders for reconstitutable delivery systems include vehicles such as suspending agents (e.g., gums, zanthans, cellulosics and sugars), humectants (e.g., sorbitol), solubilizers (e.g., ethanol, water, PEG and propylene glycol), surfactants (e.g., sodium lauryl sulfate, Spans, Tweens, and cetyl pyridine), preservatives and antioxidants (e.g., parabens, vitamins E and C, and ascorbic acid), anti-caking agents, coating agents, and chelating agents (e.g., EDTA).

Embodiments of the Invention

This invention provides a first synthetic FSH comprising a β-FSH subunit, an α-FSH subunit and a half-life-increasing moiety, wherein the β-FSH subunit, α-FSH subunit and half-life-increasing moiety are covalently bound.

Half-life increasing moieties include, for example, a peptide containing one or more glycosylation sites. A half-life increasing moiety can also be nonpeptidyl, either in whole or in part, for example, polyethylene glycol.

In one embodiment of the instant invention, the β-FSH subunit and α-FSH subunit are bound to each other via the half-life-increasing moiety, and in a preferred embodiment, the β-FSH subunit, the α-FSH subunit and the polypeptide segment exist within a single polypeptide chain.

In one embodiment of the first synthetic FSH, the β-FSH subunit is bound at its C-terminal end to the N-terminal end of the polypeptide segment, and the polypeptide segment is bound at its C-terminal end to the N-terminal end of the α-FSH subunit. In another embodiment, the α-FSH subunit is bound at its C-terminal end to the N-terminal end of the polypeptide segment, and the polypeptide segment is bound at its C-terminal end to the N-terminal end of the β-FSH subunit. In a further embodiment, the synthetic FSH comprises the N-terminal signal sequence of either the β-FSH or α-FSH subunit.

In yet a further embodiment of the first synthetic FSH, the polypeptide segment comprises the carboxy-terminal portion of the β-hCG subunit. In the preferred embodiment, the carboxy-terminal portion of the β-hCG subunit comprises the amino acid sequence corresponding to positions 113-145 of the β-hCG subunit.

The carboxy-terminal portion of the β-hCG subunit is preferably glycosylated on one or more serine residues, constituting one or more O-linked glycosylation sites. This polypeptide segment can also comprise a region having one or more N-linked glycosylation sites.

As used herein, an "N-linked" glycosylation site includes, without limitation, asn followed by any of X-ser, X-thr and X-cys, wherein X is any amino acid except proline, and glycosylation occurs on the asn residue. In this invention, the amino acid sequence of any polypeptide situated N-terminal to, C-terminal to, or in between two N-linked sites, can be of any content and length needed to suit a particular design requirement.

The instant invention also provides a second synthetic FSH comprising a β-FSH subunit covalently bound to a polypeptide segment comprising the amino acid sequence ser-gly-ser-asn-ala-thr-gly-ser-gly-ser-asn-ala-thr-ser-gly-ser (SEQ ID NO:9). The polypeptide segment may contain one or multiple copies of the amino acid sequence.

In one embodiment of the second synthetic FSH, the β-FSH subunit is bound at its C-terminal end to the N-terminal end of the peptide segment. In another embodiment, the β-FSH subunit is bound at its N-terminal end to the C-terminal end of the polypeptide segment.

This invention also provides a third synthetic FSH comprising a β-FSH subunit, an α-FSH subunit and a polypeptide segment comprising the amino acid sequence ser-gly-ser-asn-ala-thr-gly-ser-gly-ser-asn-ala-thr-ser-gly-ser (SEQ ID NO:9), wherein the β-FSH subunit, α-FSH subunit and polypeptide segment are covalently bound.

In one embodiment of third synthetic FSH, the synthetic FSH comprises a β-FSH subunit bound at its C-terminal end to the N-terminal end of the α-FSH subunit. In another embodiment, the synthetic FSH comprises an α-FSH subunit bound at its C-terminal end to the N-terminal end of the polypeptide segment, or a β-FSH subunit bound at its C-terminal end to the N-terminal end of the polypeptide segment. Conversely, the synthetic FSH can comprise an α-FSH subunit bound at its N-terminal end to the C-terminal end of the polypeptide segment, or a β-FSH subunit bound at its N-terminal end to the C-terminal end of the polypeptide segment. In a further embodiment, the β-FSH subunit is bound at its C-terminal end to the N-terminal end of the polypeptide segment, which polypeptide segment is bound at its C-terminal end to the N-terminal end of the α-FSH subunit. In yet a further embodiment, the α-FSH subunit is bound at its C-terminal end to the N-terminal end of the β-FSH subunit. In another embodiment, the α-FSH subunit may be bound at its C-terminal end to the N-terminal end of the polypeptide segment, which polypeptide segment may be bound at its C-terminal end to the N-terminal end of the β-FSH subunit.

In certain embodiments of the instant synthetic FSHs, the glycosylation is either O-linked or N-linked glycosylation. The number of glycosylation sites may be any number, such as one, two, three, four, five, or six sites. In a preferred embodiment, each site is separated from its adjacent site by about six amino acid residues.

In an embodiment of any of the instant synthetic FSHs, the α-FSH subunit (if applicable) and β-FSH subunit are from an animal selected from the group consisting of a primate, a horse, a sheep, a bird, a bovine, a pig, a dog, a cat, and a rodent. In the preferred embodiment, the α-FSH and/or β-FSH subunit is a human subunit. In a further preferred embodiment, the α-FSH subunit (if applicable) and the β-FSH subunit exist within a single polypeptide chain along with the half-life-increasing moiety.

In a further embodiment of any of the instant synthetic FSHs, where the half-life increasing moiety is a polypeptide segment having the amino acid sequence ser-gly-ser-asn-ala-thr-gly-ser-gly-ser-asn-ala-thr-ser-gly-ser (SEQ ID NO:9), the polypeptide segment comprises one or a plurality of the amino acid sequence.

This invention also provides a pharmaceutical composition comprising one of the instant synthetic FSHs and a pharmaceutically acceptable carrier.

This invention further provides an article of manufacture comprising (a) the instant pharmaceutical composition, and (b) a label and/or instructions indicating a use of the pharmaceutical composition for the enhancement of fertility, egg production and/or spermatogenesis.

This invention provides nucleic acids encoding the instant synthetic FSH molecules, as well as expression vectors and suitable host cells for expressing said molecules. Examples of vectors include a plasmid, a cosmid, a λ phage and a yeast artificial chromosome, abbreviated "YAC". Any suitable cell system may be used to express the synthetic FSH molecules of the instant invention. For example, synthetic FSHs of the instant invention may be expressed in a bacterial cell or in a eukaryotic cell. In a preferred embodiment, a synthetic FSH is expressed in a Chinese hamster ovary cell, since this cell type provides certain advantageous post-translational protein modifications.

This invention also provides a method for producing a polypeptide that comprises growing a cell, for example a Chinese hamster ovary cell, under conditions permitting expression of the polypeptide encoded by the vector therein, and recovering the polypeptide so expressed. In a preferred embodiment, the vector encoding the polypeptide is transfected into the cells and subcultured under conditions that favor the growth of those cells which have taken up the vector. For example, the vector may contain one or more antibiotic resistance genes. Thus, medium containing the antibiotic will favor the growth of only those cells which have been transfected with the vector.

In a preferred embodiment, the polypeptide contains a signal sequence that targets the polypeptide for excretion from the cell. In a further embodiment, the excreted polypeptide may be collected, purified, and concentrated, for example by affinity chromatography, gel electrophoresis, and vacuum-assisted evaporation.

This invention also provides a method for producing a synthetic FSH, which comprises: (a) co-expressing (i) a nucleic acid which encodes an α-FSH subunit, and (ii) a nucleic acid which encodes a polypeptide comprising a β-FSH subunit and a polypeptide segment comprising the amino acid sequence ser-gly-ser-asn-ala-thr-gly-ser-gly-ser-asn-ala-thr-ser-gly-ser (SEQ ID NO:9), under conditions permitting such co-expression; and recovering the synthetic FSH so produced. In an embodiment of the instant invention, the polypeptide segment contains one or multiple copies of the amino acid sequence.

In one embodiment, the β-FSH subunit is bound at its C-terminal end to the N-terminal end of the polypeptide segment, or conversely, the β-FSH subunit is bound at its N-terminal end to the C-terminal end of the polypeptide segment.

This invention also provides a method for increasing a subject's fertility which comprises administering to the subject an amount of any of the instant synthetic FSHs effective to enhance the subject's fertility. Determining a therapeutically effective amount of the instant synthetic FSHs can be done based on animal data using routine computational methods.

In one embodiment, this method is used to enhance the efficiency of in vitro fertilization protocols. For example, a synthetic FSH of the instant invention can enhance the success of in vitro fertilization by stimulating follicular maturation and egg production in the subject.

In a preferred embodiment of the instant invention, the synthetic FSH is administered to the subject less frequently than current methods allow. For example, an FSH of the instant invention may be administered every other day, every 6 to 8 days, or weekly. The instant FSH can also be administered daily.

This invention also provides a method for increasing a subject's egg production which comprises administering to the subject an amount of a synthetic FSH of the instant invention effective to enhance the subject's egg production.

This invention further provides a method for increasing spermatogenesis in a subject through administering to the subject an amount of a synthetic FSH of the instant invention effective to enhance the subject's spermatogenesis.

As used herein, a subject can be, for example, a primate, a horse, a sheep, a bird, a bovine, a pig, a dog, a cat, or a rodent. In the preferred embodiment, the subject is a human.

Finally, this invention provides a method of increasing the half-life of a molecule in a subject, which method comprises glycosylating the molecule in a manner effective to increase the molecule's half-life.

In one embodiment, the molecule is a non-peptidyl organic molecule. In another embodiment, the molecule is a polypeptide. In a further embodiment, the glycosylation is either O-linked or N-linked glycosylation. The number and spacing of glycosylation sites is as set forth herein for the instant synthetic FSHs.

This invention is illustrated in the Experimental Details section which follows. This section is set forth to aid in an understanding of the invention but is not intended to, and should not be construed to, limit in any way the invention as set forth in the claims which follow thereafter.

Experimental Details

Synopsis

This invention provides synthetic FSHs consisting of single chain fusions of β-hFSH, the common α-subunit, and an additional peptide moiety that provides an increased serum half-life while not interfering with biological activity. The pharmacokinetics, pharmacodynamics, and in vivo bioactivity of several examples of these synthetic FSHs in female rhesus monkeys are presented herein. The results demonstrate that both the absorption and the elimination half-lives of the instant synthetic FSHs are prolonged compared with native recombinant hFSH. Importantly, the analogues tested herein also demonstrated comparable in vitro bioactivity and enhanced in vivo activity compared with native recombinant hFSH.

Five examples of long-lasting FSH analogues are presented herein. These are: β-hFSH-N2 (FIG. 1), β-hFSH-N4 (FIG. 2), β-hFSH-CTP-αhFSH (FIG. 3), β-hFSH-N2-CTP-αhFSH (FIG. 4) and β-hFSH-N4-CTP-αhFSH (FIG. 5). Schematics of the CTP and N2/N4 constructs are shown in FIGS. 6 and 7. Detailed in vitro and in vivo bioactivity, as well as pharmacokinetic and pharmacodynamic analyses, were conducted for the latter three analogues and this data is presented in the section which follows.

Methods

General

Cloning and preparation of plasmid DNA were performed with E. coli strain DH5α. Clones were grown in standard Luria-Bertani medium (LB) for purification of recombinant DNA constructs. Transformation of DH5α was performed according to standard techniques using calcium chloride.

PCR reactions were performed with Vent DNA polymerase (New England Biolabs, Beverly, Mass.) and all products of the reactions were sequenced to ensure that no mutations were introduced during the amplification.

Construction of the β-hFSH-CTP-α Fusion Protein

A 5' primer introduced a Xho I site in the same frame and adjacent to the 5' ATG of the β-hFSH cDNA sequence whereas the 3' primer introduced an in frame Bam HI site adjacent to the codon for the last residue of the mature β-FSH which eliminated the terminator codon. In a similar fashion, a cDNA encoding the carboxy-terminal peptide of hCG (residues 113-145 of the hCG β-subunit sequence) was amplified with an in-frame Bam HI site adjacent to the codon for residue 113 and an in-frame Xba I site adjacent to the codon for residue 145. These two fragments were ligated to form a contiguous Xho I-Bam HI-Xba I β-hFSH-CTP fusion without a terminator codon at the 3' end. This fusion was then ligated to a cDNA encoding the mature α-subunit, lacking the amino-terminal signal peptide but including the terminator codon, flanked by in-frame 5' Spe I and 3' Sac I sites. The final construct encodes a fusion of the β-hFSH and α-subunit with the CTP sequence as the linker sequence. This final fusion sequence was then inserted into an SV40 expression vector.

Construction of the β-hFSH-N2/N4-α Fusion Protein

The β-hFSH-N2 and -N4 constructs consist of a single polypeptide chain hFSH molecule containing the β- and α-subunits tethered by a synthetic polypeptide consisting of either one or two tandem copies of the following: Ser-Gly- Ser-Asn-Ala-Thr-Gly-Ser-Gly-Ser-Asn-Ala-Thr-Ser-Gly-Ser (SEQ ID NO: 9). β-hFSH-N2 was constructed by synthesizing two complementary DNA strands encoding the above polypeptide in one of six potential reading frames. These two DNAs were designed such that following annealing a 5' Bam HI end and a 3' Spe I end were formed. The synthetic DNA duplex was then ligated into a vector with the hFSH β- and α-subunit encoding cDNAs. The in-frame ligation of these three DNAs was accomplished by placing a Xho I site immediately preceding the start codon and replacing the terminator codon of the hFSH β-subunit with a Bam HI site. In addition, an Spe I site was placed at the 5' end and a Sac I site immediately following the terminator codon of the α-subunit. The three fragments were then inserted into an SV40-based expression vector at Xho I/Sac I sites to form the β-hFSH-N2 expression construct. To insert a second copy of the synthetic polypeptide, a Bgl II site was inserted at the end of the synthetic sequence in the β-hFSH-N2 clone immediately preceding the Spe I site. The second copy of the synthetic polypeptide was then inserted by cleaving the β-hFSH-N2 construct with Bgl II and Spe I followed by insertion of the Bam HI/Spe I ended synthetic DNA to form β-hFSH-N4. This was feasible since Bam HI and Bgl II have identical cohesive termini.

Expression of β-hFSH Constructs

An SV40 expression clone containing the fusion construct was co-transfected into Chinese hamster ovary cells (CHO-K1) along with an SV2neo clone encoding resistance to the antibiotic G418. The CHO cell transformation was performed using a standard calcium phosphate precipitate technique. Selectable media containing G418 (Gemini Bioproducts, Woodland, Calif.) was used to select transfected cells. Isolated colonies were pooled and maintained in Ham's F-12 culture medium containing 500 ug/mL G418, 10% fetal bovine serum, 100 units/mL penicillin, 100 ug/mL streptomycin, and 4 mM glutamine. Pooled colonies were subcloned in 96 well microtiter dishes and clones were isolated that secreted about 3 pmole/mL of the fusion protein. To obtain higher yields, these cells were grown in suspension cultures, which produced about 9-14 pmole/mL.

Purification of β-hFSH Constructs

Spinner bottles were seeded at $10^5$ cells/mL in CHO-S-SFM medium (Life technologies, Rockville, Md.) containing 400 ug/mL G418. Cultures generally reached a density of $2 \times 10^6$ cells/mL on day 6 or 7, and the cell supernatant was harvested on day 7 or 8. PMSF was added to the supernatant at a concentration of 0.2 mM, which was then filtered through a 0.2 μm membrane and stored at 4° C. Affinity purification of was accomplished using an A201 (α-subunit specific antibody column). The column was prepared by coupling purified A201 immunoglobulins to CNBr-Sepharose-4B according to the manufacturer's instructions (Amersham Pharmacia Biotech, Piscataway, N.J.) at a concentration of 5 mg antibody/mL Sepharose. After applying the cell supernatant, the column was washed with 50 bed volumes of PBS followed by 2 bed volumes of distilled water. The fusion protein was eluted with 3-4 bed volumes of 1 M acetic acid and immediately dried on a Speed-Vac concentrator (Savant Instruments, Holbrook, N.Y.).

In Vitro FSH Bioactivity

Bioactivity of the hFSH analogues was evaluated using Y-1 cells transfected with the FSH receptor. Y-1 cell cultures were mixed with the fusion protein and native pituitary hFSH (control) at varying concentrations and media was assayed for cAMP activity as described in Bouloux et al, 2001.

Subcutaneous Protocol

Rhesus monkeys were injected subcutaneously with the fusion protein (n=4) or r-hFSH (Follistim, Organon Inc., n=2) at a dose of 10 IU/kg. All except 1 of the monkeys in each of the two treatment groups had been ovariectomized prior to injection. Serum hFSH was assayed prior to injection and at the following intervals post-injection: 12 h, 16 h, 20 h, 24 h, 36 h, 48 h, 60 h, and every 24 hours thereafter until levels reached baseline (approximately 9 days for control animals, 19-22 days for treatment animals).

Intravenous (IV) Protocol

One rhesus monkey was given an IV bolus of the fusion protein (10 IU/kg). A second animal was given an IV bolus of the control, r-hFSH at the same dose. Serum was assayed for hFSH prior to bolus administration and at the following intervals post-injection: 0.5 h, 1 h, 2 h, 4 h, 8 h, 12 h, 24 h, 36 h, 48 h, 72 h, 96 h, 120 h, 144 h and 168 h.

Pharmacokinetics

Recombinant human FSH (r-hFSH) (Follistim, Organon Inc, West Orange, N.J.) was used as a control. The Immulite assay (Diagnostic Products Corporation, Los Angeles, Calif.) was used to quantitate hFSH protein. This assay was able to detect the hFSH analogues in vitro and in vivo, and did not cross-react with rhesus FSH.

Pharmacokinetic Analysis

Each individual data set was evaluated by the pharmacokinetic data analysis program PKAnalyst (Micromath, Inc., Salt Lake City, Utah). For the IV dosing study, the following biexponential equation was fitted to the data: $C(t)=Ae-at+Be-bt$, where $C(t)$ is the plasma concentration at time "t", and A and B are the multiexponential coefficients. Values of a and b represent the initial-phase disposition rate constant and the terminal-phase disposition rate constant, respectively. PKAnalyst was used to generate the best-fit critical pharmacokinetic parameters, including elimination rate constant, half-life of initial (distribution) phase ($t_{1/2a}$), half-life of terminal (elimination) phase ($t_{1/2b}$), and total area under the blood concentration-time curve (AUC).

For the subcutaneous dosing studies, the blood concentration-time data were represented by the following biexponential equation: $C(t)=A(e-Ket-e-Kat)$, where $C(t)$ is the blood concentration at time "t" and A the multiexponential coefficient. Ke and Ka represent the elimination rate constant and absorption rate constant, respectively. All parameter estimates were computed by PKAnalyst. Bioavailability of r-hFSH and the hFSH analogues were estimated from the ratio of AUC (SC)/AUC (IV), at a constant dose (10 IU/kg).

In Vivo FSH Bioactivity

Ganirelix Acetate (250 μg) was administered by SC injection for 10 consecutive days to two normally cycling Rhesus monkeys beginning menstrual cycle day 4. The hFSH analogue was administered as a single subcutaneous dose (10 IU/kg) on cycle day 6. Venipuncture was performed daily and serum assayed for estradiol levels from cycle day 2 through cycle day 14. Serum estradiol was measured using an automated Immulite assay (Diagnostic Products Corporation, Los Angeles, Calif.).

Alternatively, hypophysectomized mice (surgery at 19 days) were purchased from the Charles River Company (Wilmington, Mass.). Upon arrival, mice were rehydrated with glucose-supplemented water for four days and randomized into control and experimental groups. Control recombinant hFSH protein or hFSH analogue was administered via a single subcutaneous injection in a total volume of 100 microliters at a dose of 10 IU. On day four post-injection, the animals were weighed and sacrificed by carbon dioxide asphyxiation followed by cardiopuncture and drainage. The uterus and ovaries were weighed and sectioned for histologic analysis.

Histologic Preparation and Follicle Counts

Both ovaries were removed from each animal. One ovary was weighed, immersed in formalin for fixation and embedded in paraffin according to standard protocols. Sections were cut at four to five micron intervals and every tenth section was stained with hematoxylin and eosin. Follicle density and maturation were assessed using the method of Pedersen and Peters (1968).

EXAMPLE 1

The β-hFSH-CTP-α Fusion Protein

In Vitro Bioactivity

Figure 8:
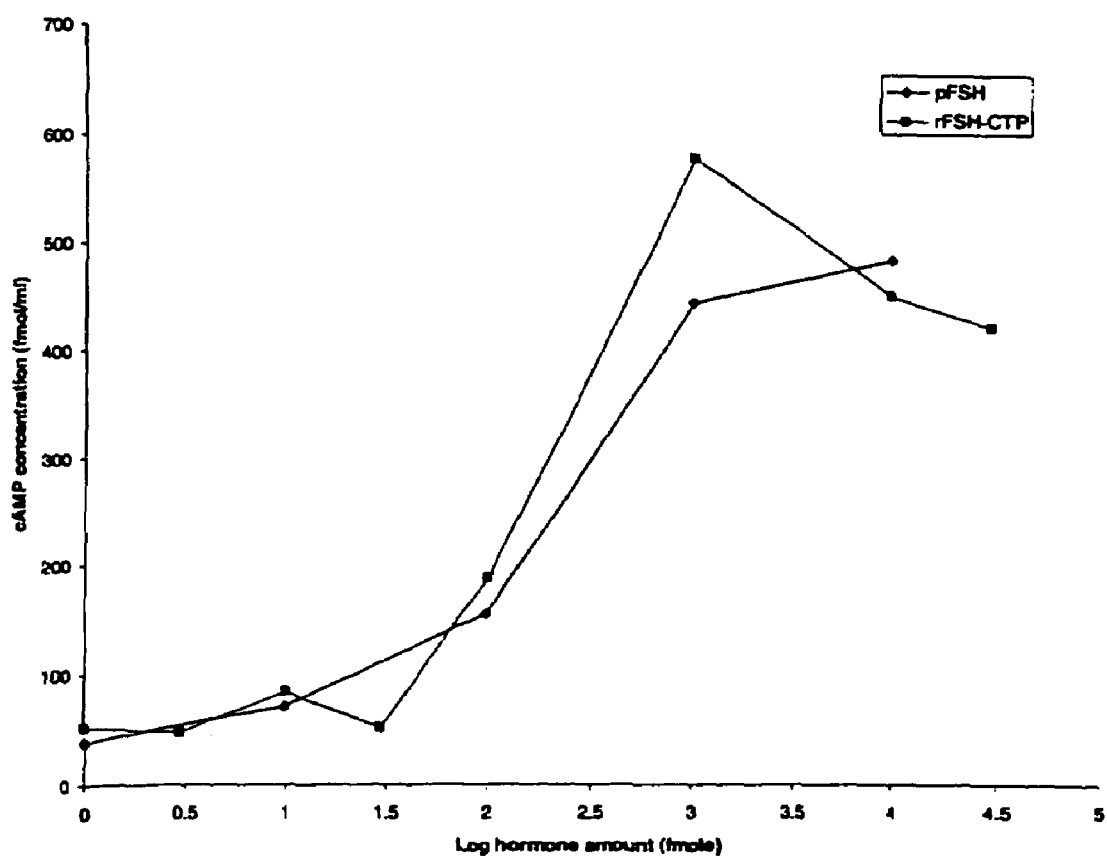
FIG. 8: In vitro bioassay of hormone activity. cAMP concentration (fmol/ml) was quantitated in Y1 cells expressing the FSH receptor after treatment with the indicated amount of either pituitary FSH (PFSH) or the FSH analogue, β-hFSH-CTP-α-hFSH (rFSH-CTP).

The bioactivity of the β-hFSH-CTP-α analogue was first assessed by an assay of hFSH receptor activity. In this assay, a recombinant native hFSH receptor is expressed in a suitable host cell and cAMP induction is measured following incubation with hormone (Lindau-Shepard et al, 2001). As shown in FIG. 8, the β-hFSH-CTP-α analogue induced a similar rise in cAMP levels when compared with recombinant hFSH, demonstrating that this single-chain fusion analogue folded properly into an unhindered, biologically active hormone.

Pharmacokinetics

In order to establish the pharmacokinetic parameters of the instant synthetic FSH, Rhesus monkeys were injected with an IV bolus dose (10 IU/kg) of either a recombinant native hFSH, or the β-hFSH-CTP-α analogue. The serum concentration of hFSH was determined by immunoassay at times following injection and a serum concentration-time curve was generated based on the data. For both the recombinant native hFSH and the β-hFSH-CTP-α analogue, the resulting curve fit a two-compartment model, consisting of an initial distribution half-life and a second, slower, elimination half-life. As indicated by the pharmacokinetic parameter estimates listed in FIG. 12, the half-life of elimination for the β-hFSH-CTP-α analogue was more than four-fold longer than that of the native hFSH.

Figure 9:
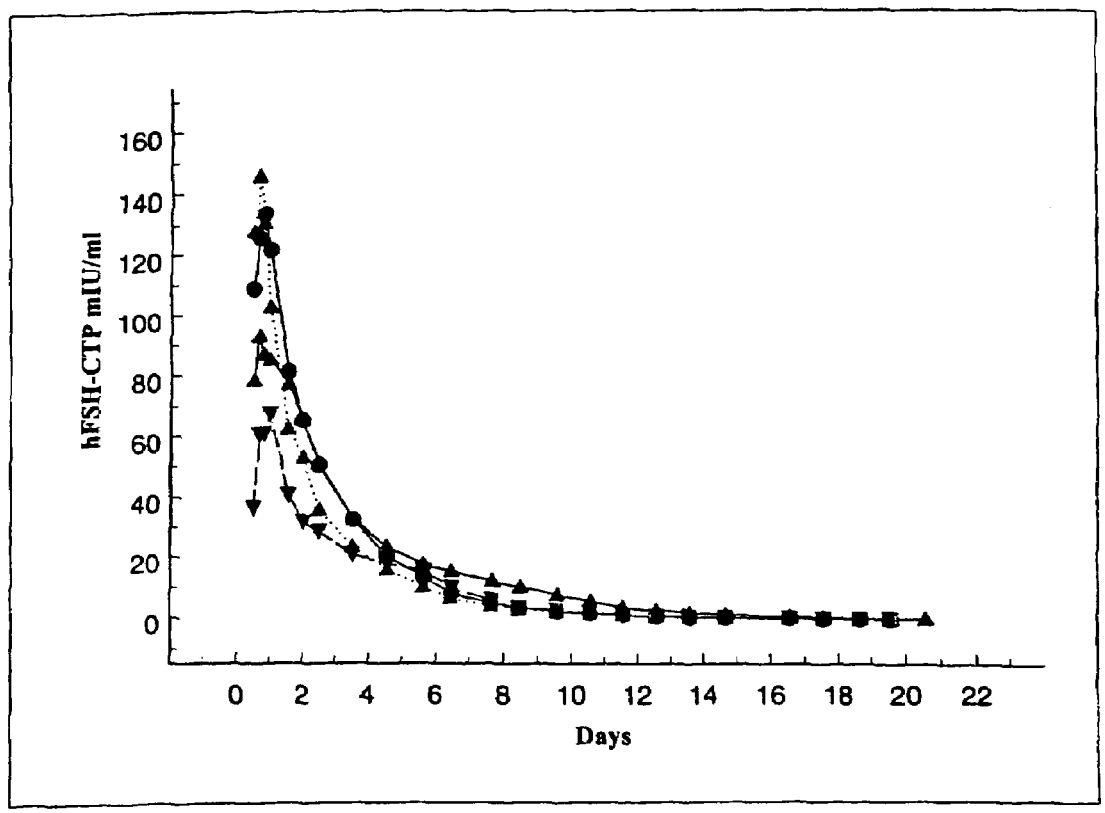
FIG. 9: Serum levels of the FSH analogue, β-hFSH-CTP-α-hFSH (hFSH-CTP), in 4 rhesus monkeys (indicated by triangles, inverted triangles, circles, and squares, respectively) measured at the indicated times following a single subcutaneous injection at a dose of 10 IU/kg.
Figure 10:
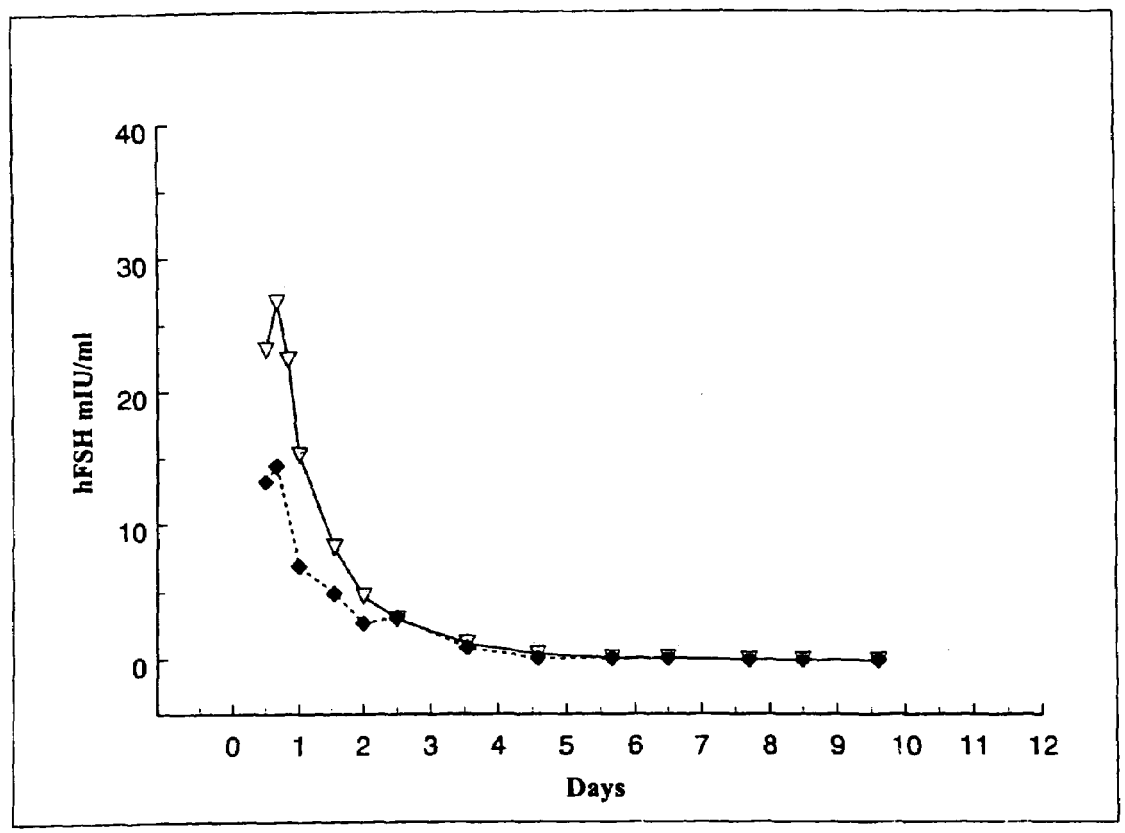
FIG. 10: Serum levels of the control recombinant hFSH protein, (hFSH), in 2 rhesus monkeys (indicated by diamonds and triangles, respectively) measured at the indicated times following a single subcutaneous injection at a dose of 10 IU/kg.

Although these results obtained following an intravenous bolus injection were encouraging, it was also important to determine the pharmacokinetic parameters of the synthetic FSH following a subcutaneous injection. This is because subcutaneous administration is a relatively easier route for clinical use. As indicated by the serum concentration-time curves for treatment animals (n=4) receiving the β-hFSH-CTP-α analogue (FIG. 9) and controls (n=2) receiving native hFSH (FIG. 10), the serum levels of native hFSH approached baseline by day 4 post-injection, whereas elevated (>2 mIU/mL) levels of the β-hFSH-CTP-α analogue were maintained for approximately 10 days. These data fit a one-compartment pharmacokinetic model, the parameter estimates of which are given in FIG. 13. Notably, the half-life of absorption for the instant synthetic FSH was approximately threefold longer than that of the native hFSH. These results show that the half-life of elimination correlates well with the intravenous data and confirms the slower metabolism and clearance of the β-hFSH-CTP-α analogue. Addition of the CTP moiety to HFSH thus induced a depot effect, retarding the absorption of the product following subcutaneous administration. This explains the slower time to reach peak concentration ($t_{max}$) for animals receiving the β-hFSH-CTP-αanalogue. As indicated in FIG. 13, both drugs were highly bioavailable after subcutaneous administration.

In Vivo Bioactivity

Figure 11:
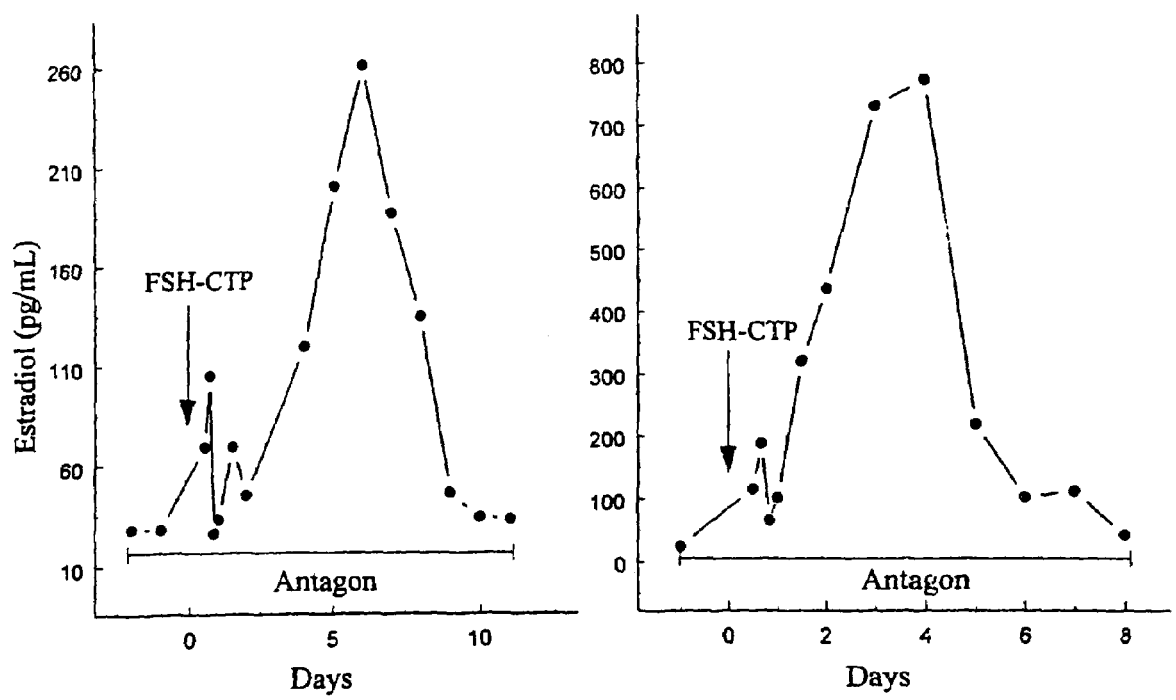
FIG. 11: Serum estradiol levels in two normally cycling monkeys following a single subcutaneous injection of the FSH analogue, β-hFSH-CTP-α-hFSH (FSH-CTP). The time of injection is indicated by arrows. Both monkeys were given the GnRH antagonist Ganirelix Acetate for the duration of the study.

To establish the bioactivity of the β-hFSH-CTP-α analogue in vivo, two normally cycling monkeys were injected with a single dose of the analogue, and serum was assayed for estradiol at various times following injection. Both monkeys were given a GnRH antagonist (Antagon, Organon, West Orange, N.J.) for the duration of the study, eliminating any effect on ovarian estrogen production from endogenous Rhesus FSH. As shown in FIG. 11, serum estradiol levels initially increased in both animals, with peak levels achieved at 3 and 5 days post-injection. One monkey attained supraphysiologic levels of estradiol (peak 773 pg/mL) on day 4 post-injection, suggesting early recruitment of multiple follicles. Thus, the β-hFSH-CTP-α analogue demonstrated similar, and in one case substantially increased, in vivo biological activity compared to native hFSH.

Conclusions

The results presented herein demonstrate that the addition of CTP to the carboxy terminus of the β subunit of hFSH had no adverse impact on folding of the molecule, receptor binding, or in vitro signal transduction. Furthermore, the fusion protein was metabolized at a slower rate than the native hormone, as circulating levels remained elevated for an extended period of time compared to native recombinant hFSH. Quantitatively, the half-life of elimination for the β-hFSH-CTP-α analogue following subcutaneous administration was 2 to 3 times longer than that of native recombinant hFSH. This difference corresponds well with the only previous report on pharmacokinetics in humans, which was done with male subjects, in which the half-life of elimination after subcutaneous administration was prolonged by a similar magnitude compared with historic controls receiving native hormone.

These results also confirm the accuracy of our parameter estimate for elimination half-life by assessing pharmacokinetics after IV administration. Surprisingly, absorption of the β-hFSH-CTP-α analogue was delayed by approximately three-fold following subcutaneous administration. The long circulating presence of the β-hFSH-CTP-α analogue after subcutaneous administration is thus explained not only by a decreased metabolism of the protein, but by a depot effect resulting in slower absorption.

In summary, the pharmacodynamics and biological activity of a β-hFSH-CTP-α analogue in a primate model are described herein for the first time. Administration of the β-hFSH-CTP-α analogue to 2 monkeys given a GnRH antagonist (to suppress endogenous FSH activity) elicited a dramatic rise in serum estradiol levels. A single subcutaneous dose resulted in elevated estradiol levels for 5-7 days, with one monkey achieving a peak estradiol level greater than 3 times that seen during a normal endogenous Rhesus cycle. This supraphysiologic response is indicative of multifollicular recruitment, although sonographic confirmation was not performed. Such prolonged elevations in estradiol are not normally seen after isolated subcutaneous injections of native recombinant hFSH.

These results confirm the feasibility of achieving prolonged ovarian stimulation following a single injection of a recombinant gonadotropin analogue. Fewer injections will result in less patient discomfort, improved compliance, and possibly a reduction in the number of local side effects.

Combination therapy using both long and short-acting FSH formulations, either together and/or sequentially during a stimulation cycle, should also be considered. In these cases, the short-acting (native) formulation may be used to "fine-tune" the FSH dose after an initial bolus of a long-acting analog.

Ideal candidates for treatment with long-acting FSH analogues include infertile males with hypogonadotropic hypogonadism, who typically require prolonged courses of gonadotropin therapy. This technology also provides a significant improvement over current methods for stimulating follicular maturation and egg production in a subject being treated for infertility and for in vitro fertilization protocols.

EXAMPLE 2

The β-hFSH-N2/N4-α Fusion Protein

In Vitro Bioactivity

The bioactivity of the β-hFSH-N2/N4-α analogues was first assessed by an assay for hFSH receptor activation as discussed above. The N2/N4 analogue induced a similar rise in cAMP levels when compared with native hFSH, demonstrating that, like the CTP analogue discussed above, this single-chain fusion protein folded properly into an unhindered, biologically active hormone.

Pharmacokinetics

Figure 20:
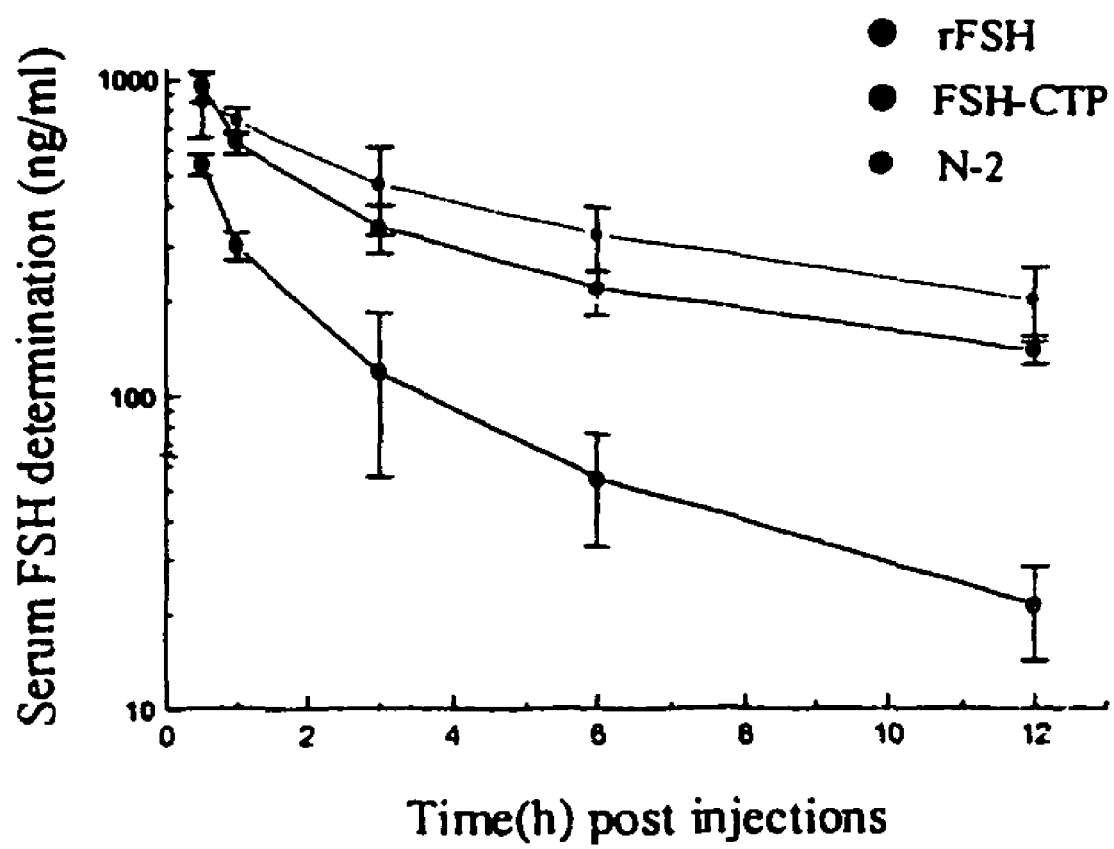
FIG. 20: Mean serum hFSH concentration-time profiles following a single IV injection of either recombinant human FSH (rFSH), FSH-CTP or N-2. Twenty-one day old female rats were injected at a dose of 2800 ng/rat.

Pharmacokinetic analysis was performed using twelve immature female rats divided into four groups of 3 each. Each of the three proteins (hFSH, hFSH-CTP, hFSH-N2) was diluted to 11 μg/ml in injection buffer containing BSA (1 mg/ml), and given as a single intravenous dose of 2800 ng/rat in 0.25 ml of buffer. The control group received 0.25 ml of saline (data not shown). Serum was assayed at the following intervals post-injection: 0.5, 1.0, 3.0, 6.0, and 12 hours. The serum concentration-time curves are shown in FIG. 20. For all products the curves could be explained by a two-compartment model, with an initial half-life reflecting the distribution phase, and a second, slower elimination half-life. As indicated by the pharmacokinetic parameter estimates in FIG. 21, the half-life of elimination for the synthetic FSHs, hFSH-CTP and hFSH-N2, was approximately two-fold longer than that of native hFSH (3.5 h vs 7.1 and 6.3 h, respectively).

In Vivo Bioactivity

Figure 19:
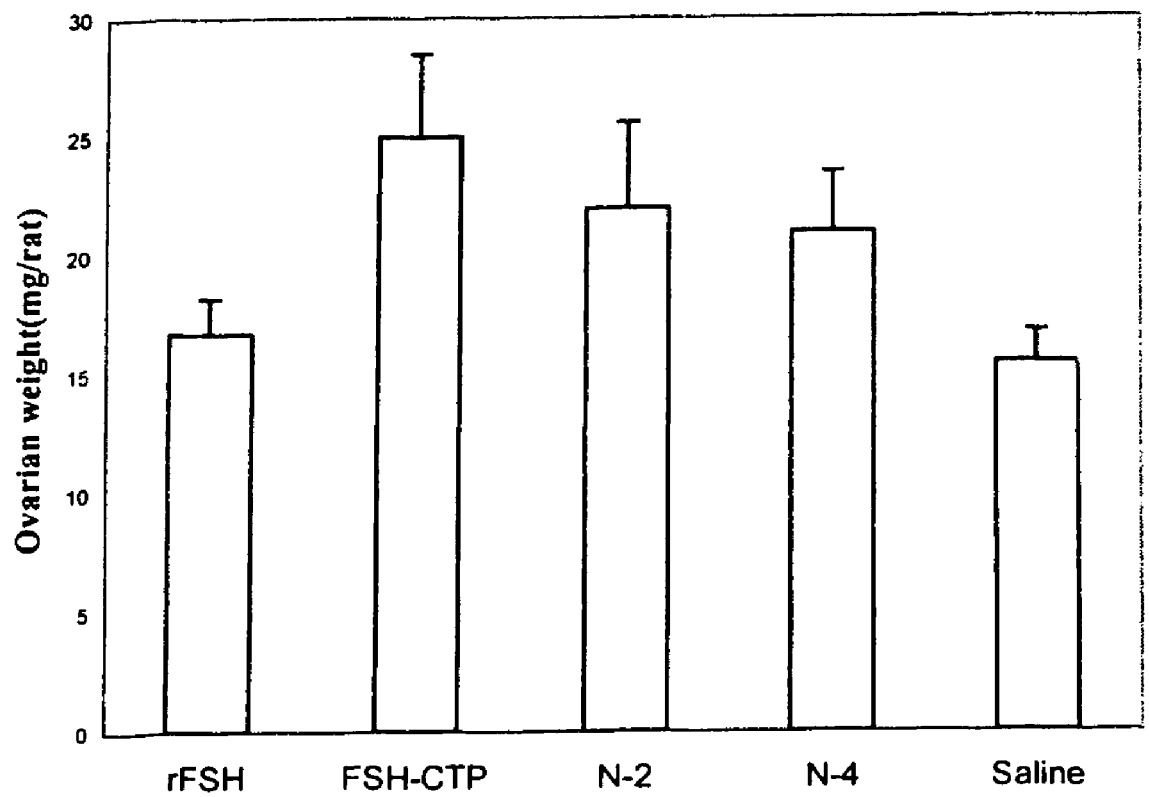
FIG. 19: Mean ovarian weight three days following subcutaneous injection of either recombinant human FSH (rFSH), FSH-CTP, N-2, N4, or saline.

An ovarian weight gain assay was used to assess the relative in vivo bioactivity of the control, recombinant native FSH (rFSH) and the CTP and N2 FSH analogues. The compounds were administered in a single subcutaneous injection. The mean ovarian weights as determined on day three following injection are shown in FIG. 19.

Pharmacodynamics

The pharmacodynamics of the N2/N4 analogues were assessed by a determination of ovarian weight change in immature female rats following a single subcutaneous injection of either a recombinant native hFSH, the CTP, the N2, or the N4 analogue. The results of these analyses are summarized in FIG. 19. The data indicated that the mean ovarian weights three days post-injection were significantly higher for the CTP, N2 and N4 analogues compared with the native hFSH control or saline.

Conclusions

The results described herein demonstrate that the addition of N-linked carbohydrates imparts a longer half-life to native hFSH, thereby increasing its bioactivity in a manner analogous to that conferred by the O-linked sugars on the CTP.

These results further demonstrate that a synthetic sequence bearing artificial N-linked glycosylation consensus sequences can be efficiently glycosylated in cultured cells. This in turn demonstrates the feasibility of producing synthetic FSH having improved stability and bioactivity through directed modifications of glycosylation patterns via the addition of artificial sequences.

REFERENCES

Bouloux, P. M., D. J. Handelsman, F. Jockenhovel, E. Nieschlag, J. Rabinovici, W. L. Frasa, J. J. de Bie, G. Voortman, and J. Itskovitz-Eldor (2001) First human exposure to FSH-CTP in hypogonadotrophic hypogonadal males. Hum. Reprod. 16, 1592-1597.

Calvo, F. O., H. T. Keutmann, E. R. Bergert, and R. J. Ryan (1986) Deglycosylated human follitropin: characterization and effects on adenosine cyclic 3',5'-phosphate production in porcine granulosa cells. Biochemistry 25, 3938-3943.

Fares, F. A., N. Suganuma, K. Nishimori, P. S. Lapolt, A. J. Hsueh, and I. Boime (1992) Design of a long-acting follitropin agonist by fusing the C-terminal sequence of the chorionic gonadotropin beta subunit to the follitropin beta subunit. Proc. Natl. Acad. Sci. U.S.A. 89, 4304-4308.

Feng, W., M. M. Matzuk, K. Mountjoy, E. Bedows, R. W. Ruddon, and I. Boime (1995) The asparagine-linked oligosaccharides of the human chorionic gonadotropin beta subunit facilitate correct disulfide bond pairing. J. Biol. Chem. 270, 11851-11859.

Krichevsky, A., S. Birken, J. F. O'Connor, K. Bikel, J. Schlatterer, and R. E. Canfield (1994) The development of a panel of monoclonal antibodies to human luteinizing hormone and its application to immunological mapping and two-site assays. Endocrine 2, 511-520.

LeContonnec, J. Y., H. C. Porchet, V. Beltrami, A. Khan, S. Toon, and M. Rowland (1994) Clinical pharmacology of recombinant human follicle-stimulating hormone. II. Single doses and steady-state pharmacokinetics. Fertil. Steril. 61, 679-86.

Lindau-Shapard, B. A., H. A. Brumberg, A. J. Peterson, and J. A. Dias (2001) Reversible immunoneutralization of human follitropin receptor. J. Reprod. Immun. 49, 1-19.

Matzuk, M. M., A. J. Hsueh, P. Lapolt, A. Tsafriri, J. L. Keene, and I. Boime (1990) The biological role of the carboxyl-terminal extension of human chorionic gonadotropin beta-subunit. Endocrinology 126, 376-383.

Pedersen, T. and H. Peters (1968) Proposal for a classification of oocytes and follicles in the mouse ovary. J. Reprod. Fertil 17, 555-557.

Pierce, J. G. and T. F. Parsons (1981) Glycoprotein hormones: structure and function. Annu. Rev. Biochem. 50, 465-495.

Porchet, H. C., J. Y. LeContonnec, B. Neuteboom, S. Canali, and G. Zanolo (1995) Pharmacokinetics of recombinant human luteinizing hormone. J. Clin. Endocrinol. Metab. 80, 667-73.

Sairam, M. R. and P. Manjunath (1982) Studies on pituitary follitropin. XL Induction of hormonal antagonistic activity by chemical deglycosylation. Mol. Cell Endocrinol. 28, 139-150.

Saal, W., H. J. Glowania, and J. Happ (1991) Pharmacodynamics and pharmacokinetics after subcutaneous and intramuscular injection of human chorionic gonado-ropin. Fertil. Steril. 56, 225-8.

Suganuma, N., M. M. Matzuk, and I. Boime (1989) Elimination of disulfide bonds affects assembly and secretion of the human chorionic gonadotropin beta subunit. J. Biol. Chem. 264, 19302-19307.

Yen, S. S., O. Llerena, B. Little, and O. H. Pearson (1968) Disappearance rates of endogenous luteinizing hormone and chorionic gonadotropin in man. J. Clin. Endocrinol. Metab 28, 1763-1767.

What is claimed is:

1. A composition comprising a polypeptide covalently bound to a serum-half-life increasing moiety, wherein the polypeptide has the sequence of an alpha subunit of follicle stimulating hormone, and wherein the serum-half-life increasing moiety comprises one or more N2 peptide sequences or N4 peptide sequences.

2. The composition of claim 1, wherein the composition is a pharmaceutical composition and comprises a pharmaceutically acceptable carrier.

3. The composition of claim 1, wherein the alpha subunit of follicle stimulating hormone is a primate, horse, sheep, bird, bovine, pig, dog, cat, or rodent alpha subunit of follicle stimulating hormone.

4. The composition of claim 1, wherein the alpha subunit of follicle stimulating hormone is a human alpha subunit of follicle stimulating hormone.

5. The composition of claim 4, wherein the human alpha subunit of follicle stimulating hormone comprises the amino acid sequence encoded by SEQ ID NO. 8.

6. The composition of claim 1, wherein the N2 peptide sequence consists of the sequence set forth in SEQ ID NO: 9.

7. The composition of claim 1, wherein the alpha subunit of follicle stimulating hormone is bound at its C-terminal end to the N-terminal end of the serum-half-life increasing moiety.

8. The composition of claim 1, wherein the alpha subunit of follicle stimulating hormone is bound at its N-terminal end to the C-terminal end of the serum-half-life increasing moiety.

* * * * *

SEQUENCE LISTING

<160> NUMBER OF SEQ ID NOS: 16

<210> SEQ ID NO 1
<211> LENGTH: 441
<212> TYPE: DNA
<213> ORGANISM: Homo sapiens
<220> FEATURE:
<221> NAME/KEY: CDS
<222> LOCATION: (1)..(438)

<400> SEQUENCE: 1

```
atg aag aca ctc cag ttt ttc ttc ctt ttc tgt tgc tgg aaa gca atc      48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa      96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc     144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa     192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga     240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg     288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt     336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa     384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca     432
Glu Gly Ser Gly Ser Asn Ala Thr Gly Ser Gly Ser Asn Ala Thr Ser
    130                 135                 140 gga tcc taa                                                         441
Gly Ser
145
```

<210> SEQ ID NO 2
<211> LENGTH: 486
<212> TYPE: DNA
<213> ORGANISM: Homo sapiens
<220> FEATURE:
<221> NAME/KEY: CDS
<222> LOCATION: (1)..(483)

<400> SEQUENCE: 2

```
atg aag aca ctc cag ttt ttc ttc ctt ttc tgt tgc tgg aaa gca atc      48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa      96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc     144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa     192
```

```
Tyr Cys Tyr Thr Arg Asp Leu Val Tyr Lys Asp Pro Ala Arg Pro Lys
         50                  55                  60 atc cag aaa aca tgt acc ttc aag gaa ctg gta tat gaa aca gtg aga      240
Ile Gln Lys Thr Cys Thr Phe Lys Glu Leu Val Tyr Glu Thr Val Arg
 65                  70                  75                  80 gtg ccc ggc tgt gct cac cat gca gat tcc ttg tat aca tac cca gtg      288
Val Pro Gly Cys Ala His His Ala Asp Ser Leu Tyr Thr Tyr Pro Val
                     85                  90                  95 gcc acc cag tgt cac tgt ggc aag tgt gac agc gac agc act gat tgt      336
Ala Thr Gln Cys His Cys Gly Lys Cys Asp Ser Asp Ser Thr Asp Cys
                    100                 105                 110 act gtg cga ggc ctg ggg ccc agc tac tgc tcc ttt ggt gaa atg aaa      384
Thr Val Arg Gly Leu Gly Pro Ser Tyr Cys Ser Phe Gly Glu Met Lys
                115                 120                 125 gaa gga tcc gga tcg aac gcg acg ggg tca ggt tct aat gca act tca      432
Glu Gly Ser Gly Ser Asn Ala Thr Gly Ser Gly Ser Asn Ala Thr Ser
            130                 135                 140 aga tcc gga tcg aac gcg acg ggg tca ggt tct aat gca act tca gga      480
Arg Ser Gly Ser Asn Ala Thr Gly Ser Gly Ser Asn Ala Thr Ser Gly
145                 150                 155                 160 tcc taa                                                              486
Ser

<210> SEQ ID NO 3
<211> LENGTH: 777
<212> TYPE: DNA
<213> ORGANISM: Homo sapiens
<220> FEATURE:
<221> NAME/KEY: CDS
<222> LOCATION: (1)..(774)

<400> SEQUENCE: 3 atg aag aca ctc cag ttt ttc ttc ctt ttc tgt tgc tgg aaa gca atc       48
Met Lys Thr Leu Gln Phe Phe Phe Leu Phe Cys Cys Trp Lys Ala Ile
  1               5                  10                  15 tgc tgc aat agc tgt gag ctg acc aac atc acc att gca ata gag aaa       96
Cys Cys Asn Ser Cys Glu Leu Thr Asn Ile Thr Ile Ala Ile Glu Lys
                 20                  25                  30 gaa gaa tgt cgt ttc tgc ata agc atc aac acc act tgg tgt gct ggc      144
Glu Glu Cys Arg Phe Cys Ile Ser Ile Asn Thr Thr Trp Cys Ala Gly
             35                  40                  45 tac tgc tac acc agg gat ctg gta tat aag gac cca gcc agg ccc aaa      192
Tyr Cys Tyr Thr Arg Asp Leu Val Tyr Lys Asp Pro Ala Arg Pro Lys
         50                  55                  60 atc cag aaa aca tgt acc ttc aag gaa ctg gta tat gaa aca gtg aga      240
Ile Gln Lys Thr Cys Thr Phe Lys Glu Leu Val Tyr Glu Thr Val Arg
 65                  70                  75                  80 gtg ccc ggc tgt gct cac cat gca gat tcc ttg tat aca tac cca gtg      288
Val Pro Gly Cys Ala His His Ala Asp Ser Leu Tyr Thr Tyr Pro Val
                     85                  90                  95 gcc acc cag tgt cac tgt ggc aag tgt gac agc gac agc act gat tgt      336
Ala Thr Gln Cys His Cys Gly Lys Cys Asp Ser Asp Ser Thr Asp Cys
                    100                 105                 110 act gtg cga ggc ctg ggg ccc agc tac tgc tcc ttt ggt gaa atg aaa      384
Thr Val Arg Gly Leu Gly Pro Ser Tyr Cys Ser Phe Gly Glu Met Lys
                115                 120                 125 gaa gga tcc ccc cgc ttc cag gac tcc tct tcc tca aag gcc cct ccc      432
Glu Gly Ser Pro Arg Phe Gln Asp Ser Ser Ser Ser Lys Ala Pro Pro
            130                 135                 140 ccc agc ctt cca agc cca tcc cga ctc ccg ggg ccc tcg gac acc ccg      480
Pro Ser Leu Pro Ser Pro Ser Arg Leu Pro Gly Pro Ser Asp Thr Pro
```

```
                  145                 150                 155                 160
atc ctc cca caa act agt gct cct gat gtg cag gat tgc cca gaa tgc       528
Ile Leu Pro Gln Thr Ser Ala Pro Asp Val Gln Asp Cys Pro Glu Cys
                165                 170                 175 acg cta cag gaa aac cca ttc ttc tcc cag ccg ggt gcc cca ata ctt       576
Thr Leu Gln Glu Asn Pro Phe Phe Ser Gln Pro Gly Ala Pro Ile Leu
            180                 185                 190 cag tgc atg ggc tgc tgc ttc tct aga gca tat ccc act cca cta agg       624
Gln Cys Met Gly Cys Cys Phe Ser Arg Ala Tyr Pro Thr Pro Leu Arg
        195                 200                 205 tcc aag aag acg atg ttg gtc caa aag aac gtc acc tca gag tcc act       672
Ser Lys Lys Thr Met Leu Val Gln Lys Asn Val Thr Ser Glu Ser Thr
    210                 215                 220 tgc tgt gta gct aaa tca tat aac agg gtc aca gta atg ggg ggt ttc       720
Cys Cys Val Ala Lys Ser Tyr Asn Arg Val Thr Val Met Gly Gly Phe
225                 230                 235                 240 aaa gtg gag aac cac acg gcg tgc cac tgc agt act tgt tat tat cac       768
Lys Val Glu Asn His Thr Ala Cys His Cys Ser Thr Cys Tyr Tyr His
                245                 250                 255 aaa tct taa                                                           777
Lys Ser <210> SEQ ID NO 4
<211> LENGTH: 723
<212> TYPE: DNA
<213> ORGANISM: Homo sapiens
<220> FEATURE:
<221> NAME/KEY: CDS
<222> LOCATION: (1)..(720)

<400> SEQUENCE: 4 atg aag aca ctc cag ttt ttc ttc ctt ttc tgt tgc tgg aaa gca atc       48
Met Lys Thr Leu Gln Phe Phe Phe Leu Phe Cys Cys Trp Lys Ala Ile
1               5                   10                  15 tgc tgc aat agc tgt gag ctg acc aac atc acc att gca ata gag aaa       96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc       144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa       192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga       240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg       288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt       336
Ala Thr Gln Cys His Cys Gly Lys Cys Asp Ser Asp Ser Thr Asp Cys
            100                 105                 110 act gtg cga ggc ctg ggg ccc agc tac tgc tcc ttt ggt gaa atg aaa       384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca       432
Glu Gly Ser Gly Ser Asn Ala Thr Gly Ser Gly Ser Asn Ala Thr Ser
    130                 135                 140 gga tcc act agt gct cct gat gtg cag gat tgc cca gaa tgc acg cta       480
Gly Ser Thr Ser Ala Pro Asp Val Gln Asp Cys Pro Glu Cys Thr Leu
145                 150                 155                 160
```

```
cag gaa aac cca ttc ttc tcc cag ccg ggt gcc cca ata ctt cag tgc      528
Gln Glu Asn Pro Phe Phe Ser Gln Pro Gly Ala Pro Ile Leu Gln Cys
                165                 170                 175 atg ggc tgc tgc ttc tct aga gca tat ccc act cca cta agg tcc aag      576
Met Gly Cys Cys Phe Ser Arg Ala Tyr Pro Thr Pro Leu Arg Ser Lys
            180                 185                 190 aag acg atg ttg gtc caa aag aac gtc acc tca gag tcc act tgc tgt      624
Lys Thr Met Leu Val Gln Lys Asn Val Thr Ser Glu Ser Thr Cys Cys
        195                 200                 205 gta gct aaa tca tat aac agg gtc aca gta atg ggg ggt ttc aaa gtg      672
Val Ala Lys Ser Tyr Asn Arg Val Thr Val Met Gly Gly Phe Lys Val
    210                 215                 220 gag aac cac acg gcg tgc cac tgc agt act tgt tat tat cac aaa tct      720
Glu Asn His Thr Ala Cys His Cys Ser Thr Cys Tyr Tyr His Lys Ser
225                 230                 235                 240 taa                                                                  723

<210> SEQ ID NO 5
<211> LENGTH: 768
<212> TYPE: DNA
<213> ORGANISM: Homo sapiens
<220> FEATURE:
<221> NAME/KEY: CDS
<222> LOCATION: (1)..(765)

<400> SEQUENCE: 5 atg aag aca ctc cag ttt ttc ttc ctt ttc tgt tgc tgg aaa gca atc       48
Met Lys Thr Leu Gln Phe Phe Phe Leu Phe Cys Cys Trp Lys Ala Ile
1               5                  10                  15 tgc tgc aat agc tgt gag ctg acc aac atc acc att gca ata gag aaa       96
Cys Cys Asn Ser Cys Glu Leu Thr Asn Ile Thr Ile Ala Ile Glu Lys
            20                  25                  30 gaa gaa tgt cgt ttc tgc ata agc atc aac acc act tgg tgt gct ggc      144
Glu Glu Cys Arg Phe Cys Ile Ser Ile Asn Thr Thr Trp Cys Ala Gly
        35                  40                  45 tac tgc tac acc agg gat ctg gtg tat aag gac cca gcc agg ccc aaa      192
Tyr Cys Tyr Thr Arg Asp Leu Val Tyr Lys Asp Pro Ala Arg Pro Lys
    50                  55                  60 atc cag aaa aca tgt acc ttc aag gaa ctg gta tat gaa aca gtg aga      240
Ile Gln Lys Thr Cys Thr Phe Lys Glu Leu Val Tyr Glu Thr Val Arg
65                  70                  75                  80 gtg ccc ggc tgt gct cac cat gca gat tcc ttg tat aca tac cca gtg      288
Val Pro Gly Cys Ala His His Ala Asp Ser Leu Tyr Thr Tyr Pro Val
                85                  90                  95 gcc acc cag tgt cac tgt ggc aag tgt gac agc gac agc act gat tgt      336
Ala Thr Gln Cys His Cys Gly Lys Cys Asp Ser Asp Ser Thr Asp Cys
            100                 105                 110 act gtg cga ggc ctg ggg cca agc tac tgc tcc ttt ggt gaa atg aaa      384
Thr Val Arg Gly Leu Gly Pro Ser Tyr Cys Ser Phe Gly Glu Met Lys
        115                 120                 125 gaa gga tcc gga tcg aac gcg acg ggg tca ggt tct aat gca act tca      432
Glu Gly Ser Gly Ser Asn Ala Thr Gly Ser Gly Ser Asn Ala Thr Ser
    130                 135                 140 aga tcc gga tcg aac gcg acg ggg tca ggt tct aat gca act tca gga      480
Arg Ser Gly Ser Asn Ala Thr Gly Ser Gly Ser Asn Ala Thr Ser Gly
145                 150                 155                 160 tcc act agt gct cct gat gtg cag gat tgc cca gaa tgc acg cta cag      528
Ser Thr Ser Ala Pro Asp Val Gln Asp Cys Pro Glu Cys Thr Leu Gln
                165                 170                 175 gaa aac cca ttc ttc tcc cag ccg ggt gcc cca ata ctt cag tgc atg      576
Glu Asn Pro Phe Phe Ser Gln Pro Gly Ala Pro Ile Leu Gln Cys Met
```

```
                                                                                  624
ggc tgc tgc ttc tct aga gca tat ccc act cca cta agg tcc aag aag
Gly Cys Cys Phe Ser Arg Ala Tyr Pro Thr Pro Leu Arg Ser Lys Lys
        195                 200                 205

672
acg atg ttg gtc caa aag aac gtc acc tca gag tcc act tgc tgt gta
Thr Met Leu Val Gln Lys Asn Val Thr Ser Glu Ser Thr Cys Cys Val
    210                 215                 220

720
gct aaa tca tat aac agg gtc aca gta atg ggg ggt ttc aaa gtg gag
Ala Lys Ser Tyr Asn Arg Val Thr Val Met Gly Gly Phe Lys Val Glu
225                 230                 235                 240

768
aac cac acg gcg tgc cac tgc agt act tgt tat tat cac aaa tct taa
Asn His Thr Ala Cys His Cys Ser Thr Cys Tyr Tyr His Lys Ser
                245                 250                 255
```

<210> SEQ ID NO 6
<211> LENGTH: 145
<212> TYPE: PRT
<213> ORGANISM: Homo sapiens

<400> SEQUENCE: 6

```
Ser Lys Glu Pro Leu Arg Pro Arg Cys Arg Pro Ile Asn Ala Thr Leu
1               5                   10                  15

Ala Val Glu Lys Glu Gly Cys Pro Val Cys Ile Thr Val Asn Thr Thr
            20                  25                  30

Ile Cys Ala Gly Tyr Cys Pro Thr Met Thr Arg Val Leu Gln Gly Val
        35                  40                  45

Leu Pro Ala Leu Pro Gln Val Val Cys Asn Tyr Arg Asp Val Arg Phe
    50                  55                  60

Glu Ser Ile Arg Leu Pro Gly Cys Pro Arg Gly Val Asn Pro Val Val
65                  70                  75                  80

Ser Tyr Ala Val Ala Leu Ser Cys Gln Cys Ala Leu Cys Arg Arg Ser
                85                  90                  95

Thr Thr Asp Cys Gly Gly Pro Lys Asp His Pro Leu Thr Cys Asp Asp
            100                 105                 110

Pro Arg Phe Gln Asp Ser Ser Ser Lys Ala Pro Pro Pro Ser Leu
        115                 120                 125

Pro Ser Pro Ser Arg Leu Pro Gly Pro Ser Asp Thr Pro Ile Leu Pro
    130                 135                 140

Gln
145
```

<210> SEQ ID NO 7
<211> LENGTH: 390
<212> TYPE: DNA
<213> ORGANISM: Homo sapiens
<220> FEATURE:
<221> NAME/KEY: CDS
<222> LOCATION: (1)..(387)

<400> SEQUENCE: 7

```
                                                                                   48
atg aag aca ctc cag ttt ttc ttc ctt ttc tgt tgc tgg aaa gca atc
Met Lys Thr Leu Gln Phe Phe Phe Leu Phe Cys Cys Trp Lys Ala Ile
1               5                   10                  15

96
tgc tgc aat agc tgt gag ctg acc aac atc acc att gca ata gag aaa
Cys Cys Asn Ser Cys Glu Leu Thr Asn Ile Thr Ile Ala Ile Glu Lys
            20                  25                  30

144
gaa gaa tgt cgt ttc tgc ata agc atc aac acc act tgg tgt gct ggc
Glu Glu Cys Arg Phe Cys Ile Ser Ile Asn Thr Thr Trp Cys Ala Gly
        35                  40                  45
```

```
tac tgc tac acc agg gat ctg gtg tat aag gac cca gcc agg ccc aaa      192
Tyr Cys Tyr Thr Arg Asp Leu Val Tyr Lys Asp Pro Ala Arg Pro Lys
 50                  55                  60 atc cag aaa aca tgt acc ttc aag gaa ctg gta tat gaa aca gtg aga      240
Ile Gln Lys Thr Cys Thr Phe Lys Glu Leu Val Tyr Glu Thr Val Arg
 65                  70                  75                  80 gtg ccc ggc tgt gct cac cat gca gat tcc ttg tat aca tac cca gtg      288
Val Pro Gly Cys Ala His His Ala Asp Ser Leu Tyr Thr Tyr Pro Val
                 85                  90                  95 gcc acc cag tgt cac tgt ggc aag tgt gac agc gac agc act gat tgt      336
Ala Thr Gln Cys His Cys Gly Lys Cys Asp Ser Asp Ser Thr Asp Cys
            100                 105                 110 act gtg cga ggc ctg ggg ccc agc tac tgt tcc ttt ggt gaa atg aaa      384
Thr Val Arg Gly Leu Gly Pro Ser Tyr Cys Ser Phe Gly Glu Met Lys
        115                 120                 125 gaa taa                                                              390
Glu

<210> SEQ ID NO 8
<211> LENGTH: 351
<212> TYPE: DNA
<213> ORGANISM: Homo sapiens
<220> FEATURE:
<221> NAME/KEY: CDS
<222> LOCATION: (1)..(348)

<400> SEQUENCE: 8 atg gat tac tac aga aaa tat gca gct atc ttt ctg gtc aca ttg tcg       48
Met Asp Tyr Tyr Arg Lys Tyr Ala Ala Ile Phe Leu Val Thr Leu Ser
  1               5                  10                  15 gtg ttt ctg cat gtt ctc cat tcc gct cct gat gtg cag gat tgc cca       96
Val Phe Leu His Val Leu His Ser Ala Pro Asp Val Gln Asp Cys Pro
                 20                  25                  30 gaa tgc acg cta cag gaa aac cca ttc ttc tcc cag ccg ggt gcc cca      144
Glu Cys Thr Leu Gln Glu Asn Pro Phe Phe Ser Gln Pro Gly Ala Pro
             35                  40                  45 ata ctt cag tgc atg ggc tgc tgc ttc tct aga gca tat ccc act cca      192
Ile Leu Gln Cys Met Gly Cys Cys Phe Ser Arg Ala Tyr Pro Thr Pro
 50                  55                  60 cta agg tcc aag aag acg atg ttg gtc caa aag aac gtc acc tca gag      240
Leu Arg Ser Lys Lys Thr Met Leu Val Gln Lys Asn Val Thr Ser Glu
 65                  70                  75                  80 tcc act tgc tgt gta gct aaa tca tat aac agg gtc aca gta atg ggg      288
Ser Thr Cys Cys Val Ala Lys Ser Tyr Asn Arg Val Thr Val Met Gly
                 85                  90                  95 ggt ttc aaa gtg gag aac cac acg gcg tgc cac tgc agt act tgt tat      336
Gly Phe Lys Val Glu Asn His Thr Ala Cys His Cys Ser Thr Cys Tyr
            100                 105                 110 tat cac aaa tct taa                                                  351
Tyr His Lys Ser
        115

<210> SEQ ID NO 9
<211> LENGTH: 16
<212> TYPE: PRT
<213> ORGANISM: Homo sapiens

<400> SEQUENCE: 9

Ser Gly Ser Asn Ala Thr Gly Ser Gly Ser Asn Ala Thr Ser Gly Ser
  1               5                  10                  15
```

<210> SEQ ID NO 10
<211> LENGTH: 146
<212> TYPE: PRT
<213> ORGANISM: Homo sapiens

<400> SEQUENCE: 10

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
                35                  40                  45

Tyr Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
                115                 120                 125

Glu Gly Ser Gly Ser Asn Ala Thr Gly Ser Gly Ser Asn Ala Thr Ser
    130                 135                 140

Gly Ser
145
```

<210> SEQ ID NO 11
<211> LENGTH: 161
<212> TYPE: PRT
<213> ORGANISM: Homo sapiens

<400> SEQUENCE: 11

```
Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
                35                  40                  45

Tyr Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
                100                 105                 110

Thr Val Arg Gly Leu Gly Pro Ser Tyr Cys Ser Phe Gly Glu Met Lys
                115                 120                 125

Glu Gly Ser Gly Ser Asn Ala Thr Gly Ser Gly Ser Asn Ala Thr Ser
    130                 135                 140

Arg Ser Gly Ser Asn Ala Thr Gly Ser Gly Ser Asn Ala Thr Ser Gly
145                 150                 155                 160

Ser
```

<210> SEQ ID NO 12

<211> LENGTH: 258
<212> TYPE: PRT
<213> ORGANISM: Homo sapiens

<400> SEQUENCE: 12

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu Gly Ser Pro Arg Phe Gln Asp Ser Ser Ser Lys Ala Pro Pro
130                 135                 140

Pro Ser Leu Pro Ser Pro Ser Arg Leu Pro Gly Pro Ser Asp Thr Pro
145                 150                 155                 160

Ile Leu Pro Gln Thr Ser Ala Pro Asp Val Gln Asp Cys Pro Glu Cys
                165                 170                 175

Thr Leu Gln Glu Asn Pro Phe Phe Ser Gln Pro Gly Ala Pro Ile Leu
            180                 185                 190

Gln Cys Met Gly Cys Cys Phe Ser Arg Ala Tyr Pro Thr Pro Leu Arg
        195                 200                 205

Ser Lys Lys Thr Met Leu Val Gln Lys Asn Val Thr Ser Glu Ser Thr
210                 215                 220

Cys Cys Val Ala Lys Ser Tyr Asn Arg Val Thr Val Met Gly Gly Phe
225                 230                 235                 240

Lys Val Glu Asn His Thr Ala Cys His Cys Ser Thr Cys Tyr Tyr His
                245                 250                 255

Lys Ser

<210> SEQ ID NO 13
<211> LENGTH: 240
<212> TYPE: PRT
<213> ORGANISM: Homo sapiens

<400> SEQUENCE: 13

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
        35                  40                  45

Tyr Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

```
Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu Gly Ser Gly Ser Asn Ala Thr Gly Ser Gly Ser Asn Ala Thr Ser
            130                 135                 140

Gly Ser Thr Ser Ala Pro Asp Val Gln Asp Cys Pro Glu Cys Thr Leu
145                 150                 155                 160

Gln Glu Asn Pro Phe Phe Ser Gln Pro Gly Ala Pro Ile Leu Gln Cys
                165                 170                 175

Met Gly Cys Cys Phe Ser Arg Ala Tyr Pro Thr Pro Leu Arg Ser Lys
            180                 185                 190

Lys Thr Met Leu Val Gln Lys Asn Val Thr Ser Glu Ser Thr Cys Cys
        195                 200                 205

Val Ala Lys Ser Tyr Asn Arg Val Thr Val Met Gly Gly Phe Lys Val
    210                 215                 220

Glu Asn His Thr Ala Cys His Cys Ser Thr Cys Tyr Tyr His Lys Ser
225                 230                 235                 240

<210> SEQ ID NO 14
<211> LENGTH: 255
<212> TYPE: PRT
<213> ORGANISM: Homo sapiens

<400> SEQUENCE: 14

Met Lys Thr Leu Gln Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
            20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
    50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
            85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
            115                 120                 125

Glu Gly Ser Gly Ser Asn Ala Thr Gly Ser Gly Ser Asn Ala Thr Ser
            130                 135                 140

Arg Ser Gly Ser Asn Ala Thr Gly Ser Gly Ser Asn Ala Thr Ser Gly
145                 150                 155                 160

Ser Thr Ser Ala Pro Asp Val Gln Asp Cys Pro Glu Cys Thr Leu Gln
                165                 170                 175

Glu Asn Pro Phe Phe Ser Gln Pro Gly Ala Pro Ile Leu Gln Cys Met
            180                 185                 190

Gly Cys Cys Phe Ser Arg Ala Tyr Pro Thr Pro Leu Arg Ser Lys Lys
        195                 200                 205

Thr Met Leu Val Gln Lys Asn Val Thr Ser Glu Ser Thr Cys Cys Val
    210                 215                 220
```

```
Ala Lys Ser Tyr Asn Arg Val Thr Val Met Gly Gly Phe Lys Val Glu
225                 230                 235                 240

Asn His Thr Ala Cys His Cys Ser Thr Cys Tyr Tyr His Lys Ser
                245                 250                 255

<210> SEQ ID NO 15
<211> LENGTH: 129
<212> TYPE: PRT
<213> ORGANISM: Homo sapiens

<400> SEQUENCE: 15

Met Lys Thr Leu Gln Phe Phe Phe Leu Phe Cys Cys Trp Lys Ala Ile
1               5                   10                  15

Cys Cys Asn Ser Cys Glu Leu Thr Asn Ile Thr Ile Ala Ile Glu Lys
                20                  25                  30

Glu Glu Cys Arg Phe Cys Ile Ser Ile Asn Thr Thr Trp Cys Ala Gly
            35                  40                  45

Tyr Cys Tyr Thr Arg Asp Leu Val Tyr Lys Asp Pro Ala Arg Pro Lys
50                  55                  60

Ile Gln Lys Thr Cys Thr Phe Lys Glu Leu Val Tyr Glu Thr Val Arg
65                  70                  75                  80

Val Pro Gly Cys Ala His His Ala Asp Ser Leu Tyr Thr Tyr Pro Val
                85                  90                  95

Ala Thr Gln Cys His Cys Gly Lys Cys Asp Ser Asp Ser Thr Asp Cys
            100                 105                 110

Thr Val Arg Gly Leu Gly Pro Ser Tyr Cys Ser Phe Gly Glu Met Lys
        115                 120                 125

Glu

<210> SEQ ID NO 16
<211> LENGTH: 116
<212> TYPE: PRT
<213> ORGANISM: Homo sapiens

<400> SEQUENCE: 16

Met Asp Tyr Tyr Arg Lys Tyr Ala Ala Ile Phe Leu Val Thr Leu Ser
1               5                   10                  15

Val Phe Leu His Val Leu His Ser Ala Pro Asp Val Gln Asp Cys Pro
                20                  25                  30

Glu Cys Thr Leu Gln Glu Asn Pro Phe Phe Ser Gln Pro Gly Ala Pro
            35                  40                  45

Ile Leu Gln Cys Met Gly Cys Cys Phe Ser Arg Ala Tyr Pro Thr Pro
50                  55                  60

Leu Arg Ser Lys Lys Thr Met Leu Val Gln Lys Asn Val Thr Ser Glu
65                  70                  75                  80

Ser Thr Cys Cys Val Ala Lys Ser Tyr Asn Arg Val Thr Val Met Gly
                85                  90                  95

Gly Phe Lys Val Glu Asn His Thr Ala Cys His Cys Ser Thr Cys Tyr
            100                 105                 110

Tyr His Lys Ser
        115
```